(12) United States Patent
Tatsutani et al.

(10) Patent No.: US 8,731,709 B2
(45) Date of Patent: May 20, 2014

(54) SAMPLE PROCESSING APPARATUS AND SAMPLE RACK TRANSPORTING METHOD

(75) Inventors: Hiroo Tatsutani, Kobe (JP); Tomoyuki Asahara, Kobe (JP); Nobuyoshi Yamakawa, Kobe (JP)

(73) Assignee: Sysmex Corporation, Chuo-ku, Kobe-shi (JP)

(*) Notice: Subject to any disclaimer, the term of this patent is extended or adjusted under 35 U.S.C. 154(b) by 479 days.

(21) Appl. No.: 12/978,851

(22) Filed: Dec. 27, 2010

(65) Prior Publication Data
US 2011/0160899 A1    Jun. 30, 2011

(30) Foreign Application Priority Data
Dec. 28, 2009   (JP) ................................ 2009-296836

(51) Int. Cl.
*B65G 49/00* (2006.01)

(52) U.S. Cl.
USPC ..................... 700/218; 73/863.91; 73/864.21; 436/43; 436/47; 209/587; 422/65

(58) Field of Classification Search
USPC ......................................................... 700/218
See application file for complete search history.

(56) References Cited

U.S. PATENT DOCUMENTS

| | | | | |
|---|---|---|---|---|
| 6,255,614 B1 * | 7/2001 | Yamakawa et al. | ........... | 209/587 |
| 7,752,007 B2 * | 7/2010 | Yamasaki et al. | ............. | 702/127 |
| 8,083,995 B2 * | 12/2011 | Tsutsumida et al. | ............ | 422/65 |

FOREIGN PATENT DOCUMENTS

| | | | | |
|---|---|---|---|---|
| JP | 09-043249 A | 2/1997 | | |
| JP | 11-094841 A | 4/1999 | | |
| JP | 2000-088860 A | 3/2000 | | |
| JP | 2000088860 | * 3/2000 | ............. | G01N 35/04 |
| JP | 2002-277477 A | 9/2002 | | |

* cited by examiner

*Primary Examiner* — Gene Crawford
*Assistant Examiner* — Kyle Logan
(74) *Attorney, Agent, or Firm* — Brinks, Gilson & Lione

(57) ABSTRACT

A sample processing apparatus comprising: a plurality of sample processing units, each processing a sample contained in a sample container; a transport apparatus that transports a sample rack holding a sample container to at least any one of the plurality of sample processing units; a rack feeding section that receives a sample rack and feeds the received sample rack to a transport line of the transport apparatus; and a controller configured to instruct the transport apparatus, according to a quantity of sample racks received by the rack feeding section, to transport a sample rack fed by the rack feeding section to either (a) a sample processing unit which can accept a subsequent sample rack more rapidly than any other sample processing unit or (b) a sample processing unit having a lower processing load than any other sample processing unit. Also, a sample rack transporting method.

19 Claims, 13 Drawing Sheets

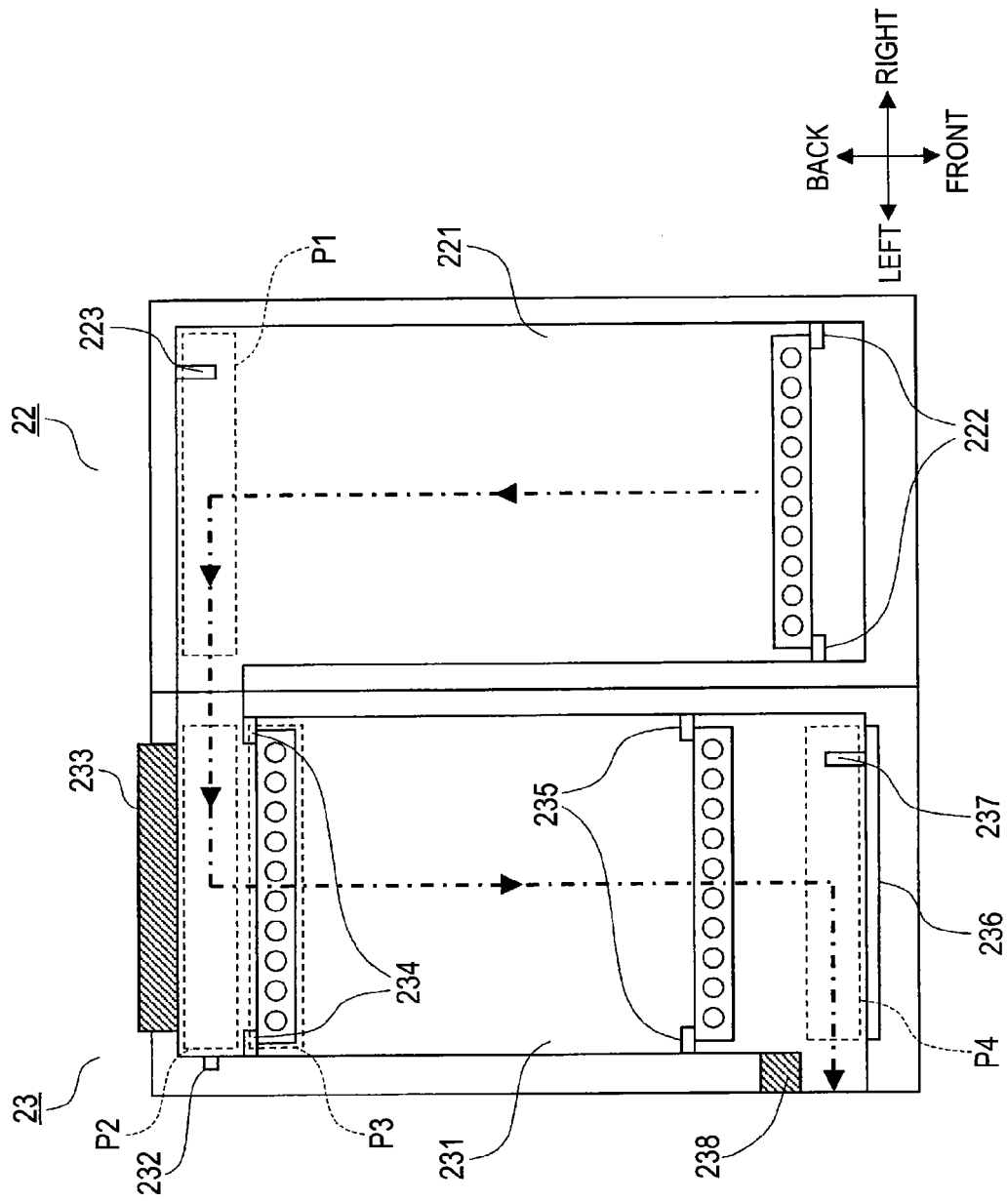

FIG.8A

| | NUMBER OF MEASUREMENTS OF MEASURING UNIT |
|---|---|
| SAMPLE TRANSPORT UNIT (1) | N1 |
| SAMPLE TRANSPORT UNIT (2) | N2 |
| SAMPLE TRANSPORT UNIT (3) | N3 |

FIG.8B

| | NUMBER OF SAMPLE RACKS OF MEASURING UNIT |
|---|---|
| SAMPLE TRANSPORT UNIT (1) | M1 |
| SAMPLE TRANSPORT UNIT (2) | M2 |
| SAMPLE TRANSPORT UNIT (3) | M3 |

FIG.8C

| | NUMBER OF MEASUREMENTS OF MEASURING UNIT | NUMBER OF SAMPLE RACKS OF MEASURING UNIT |
|---|---|---|
| SAMPLE TRANSPORT UNIT (1) | N1 | M1 |
| SAMPLE TRANSPORT UNIT (2) | N2 | M2 |
| SAMPLE TRANSPORT UNIT (3) | N3 | M3 |

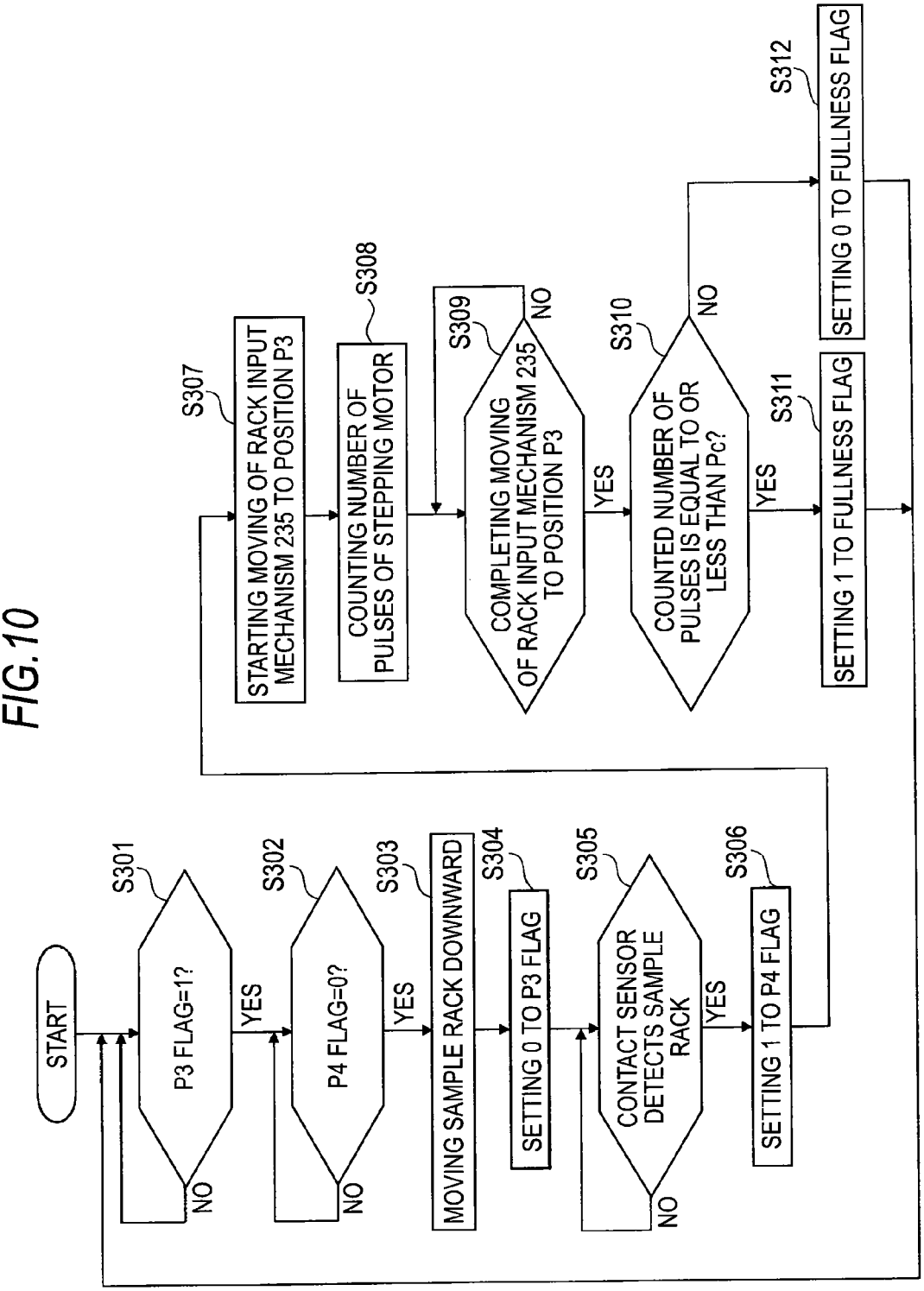

SAMPLE PROCESSING APPARATUS AND SAMPLE RACK TRANSPORTING METHOD

RELATED APPLICATIONS

This application claims priority under 35 U.S.C. §119 to Japanese Patent Application No. 2009-296836 filed on Dec. 28, 2009, the entire content of which is hereby incorporated by reference.

BACKGROUND OF THE INVENTION

1. Field of the Invention

The present invention relates to a sample processing apparatus having a plurality of sample processing units and a sample rack transporting method for transporting sample racks to the plurality of processing units.

2. Description of the Related Art

Currently, sample analysis apparatuses for processing clinical samples, such as blood or urine, are used in medical institutions, such as hospitals. Some of such sample analysis apparatuses are configured to include a plurality of measuring units and a transport apparatus for transporting sample racks to the plurality of measuring units in order to improve processing capabilities.

In such sample analysis apparatuses, a measurement load tends to become overly concentrated on one measuring unit. When the measurement load becomes concentrated on one measurement unit, breakdowns or malfunctions easily occur in the measuring unit. Accordingly, in Japanese Laid-Open Patent Publication No. 2000-88860, a method for equalizing the loads on the measuring units is described. That is, in Japanese Laid-Open Patent Publication No. 2000-88860, on the basis of the status of the loads on the measuring units, it is decided whether to transport a sample rack to the measuring unit on the most upstream side, and thus the measurement loads on the measuring units are equalized.

According to the method of Japanese Laid-Open Patent Publication No. 2000-88860, a transport operation for equalizing the loads on the measuring units is uniformly performed regardless of the number of samples which have been received as measurement targets by the sample analysis apparatus. However, when the sample analysis apparatus receives a great number of samples which are measurement targets or when the congestion of the measurement is predicted, it is desirable that speediness of measurement is given higher priority than equalization of loads on the measuring units.

SUMMARY OF THE INVENTION

The scope of the present invention is defined solely by the appended claims, and is not affected to any degree by the statements within this summary.

According to a first aspect of the present invention, a sample processing apparatus comprising: a plurality of sample processing units, each processing a sample contained in a sample container; a transport apparatus that transports a sample rack holding a sample container to at least any one of the plurality of sample processing units; a rack feeding section that receives a sample rack and feeds the received sample rack to a transport line of the transport apparatus; and a controller configured to instruct the transport apparatus, according to a quantity of sample racks received by the rack feeding section, to transport a sample rack fed by the rack feeding section to either (a) a sample processing unit which can accept a subsequent sample rack more rapidly than any other sample processing unit or (b) a sample processing unit having a lower processing load than any other sample processing unit.

According to a second aspect of the present invention, a sample processing apparatus comprising: a plurality of sample processing units, each processing a sample contained in a sample container; a transport apparatus that transports a sample rack holding a sample container to at least any one of the plurality of sample processing units; a rack feeding section that receives the sample rack and feeds the received sample rack to a transport line of the transport apparatus; a receiving part which receives a selection of whether to set (i) a first transport method for transporting the sample rack fed by the rack feeding section to a sample processing unit which can accept a subsequent sample rack more rapidly than any other sample processing unit or (ii) a second transport method for transporting the sample rack fed by the rack feeding section to a sample processing unit having a lower processing load than any other sample processing unit; and a controller configured to instruct the transport apparatus to transport the sample rack fed by the rack feeding section by a transport method received by the receiving part.

According to a third aspect of the present invention, a sample processing apparatus comprising: a plurality of sample processing units, each processing a sample contained in a sample container; a transport apparatus that transports a sample rack holding a sample container to at least any one of the plurality of sample processing units; a rack feeding section that receives the sample rack and feeds the received sample rack to a transport line of the transport apparatus; and a controller configured to instruct the transport apparatus to transport a sample rack fed by the rack feeding section to (a) a sample processing unit which can accept a subsequent sample rack more rapidly than any other sample processing unit when a current time is included in a time slot in which a crowded state of sample racks set in the sample processing apparatus is severe, and to instruct the transport apparatus to transport a sample rack fed by the rack feeding section to (b) a sample processing unit having a lower processing load than any other sample processing unit when the current time is not included in the time slot.

According to a fourth aspect of the present invention, a sample rack transporting method by a sample processing apparatus comprising: receiving a sample rack holding a sample container; feeding the received sample rack to a transport line of the sample processing apparatus; transporting the fed sample rack to either (a) a sample processing unit which can accept a subsequent sample rack more rapidly than any other sample processing unit or (b) a sample processing unit having a lower processing load than any other sample processing unit, according to a quantity of the received sample racks.

According to a fifth aspect of the present invention, a sample rack transporting method by a sample processing apparatus comprising: receiving a sample rack holding a sample container; feeding the received sample rack to a transport line of the sample processing apparatus; transporting the fed sample rack to either (a) a sample processing unit which can accept a subsequent sample rack more rapidly than any other sample processing unit or (b) a sample processing unit having a lower processing load than any other sample processing unit, when the current time is included in a time slot in which a crowded state of the sample racks set in the sample processing apparatus is severe.

BRIEF DESCRIPTION OF THE DRAWINGS

FIG. 3 is a plan view showing the configurations of a sample insertion unit and a sample output unit according to the first embodiment;

FIGS. 8A to 8C include a chart showing the number of measurements of the measuring unit according to the first embodiment and a chart showing the number of sample racks transported to the measuring unit, which is used in place of the number of measurements according to a modified example of the embodiment;

FIG. 10 is a flowchart showing that a sample rack which is positioned at the rear position of the sample insertion unit according to the first embodiment is controlled to be output toward the sample transport unit;

DETAILED DESCRIPTION OF THE PREFERRED EMBODIMENTS

This embodiment is a sample analysis system for examination and analysis related to blood, to which the present invention is applied. A sample analysis system according to this embodiment includes three measuring units and one smear preparation apparatus. In the three measuring units, blood analysis is performed in parallel, and when it is necessary to prepare a smear based on the analysis result thereof, the smear preparation apparatus prepares a smear.

1. First Embodiment

Hereinafter, a sample analysis system according to a first embodiment will be described with reference to the drawings.

Figure 1:
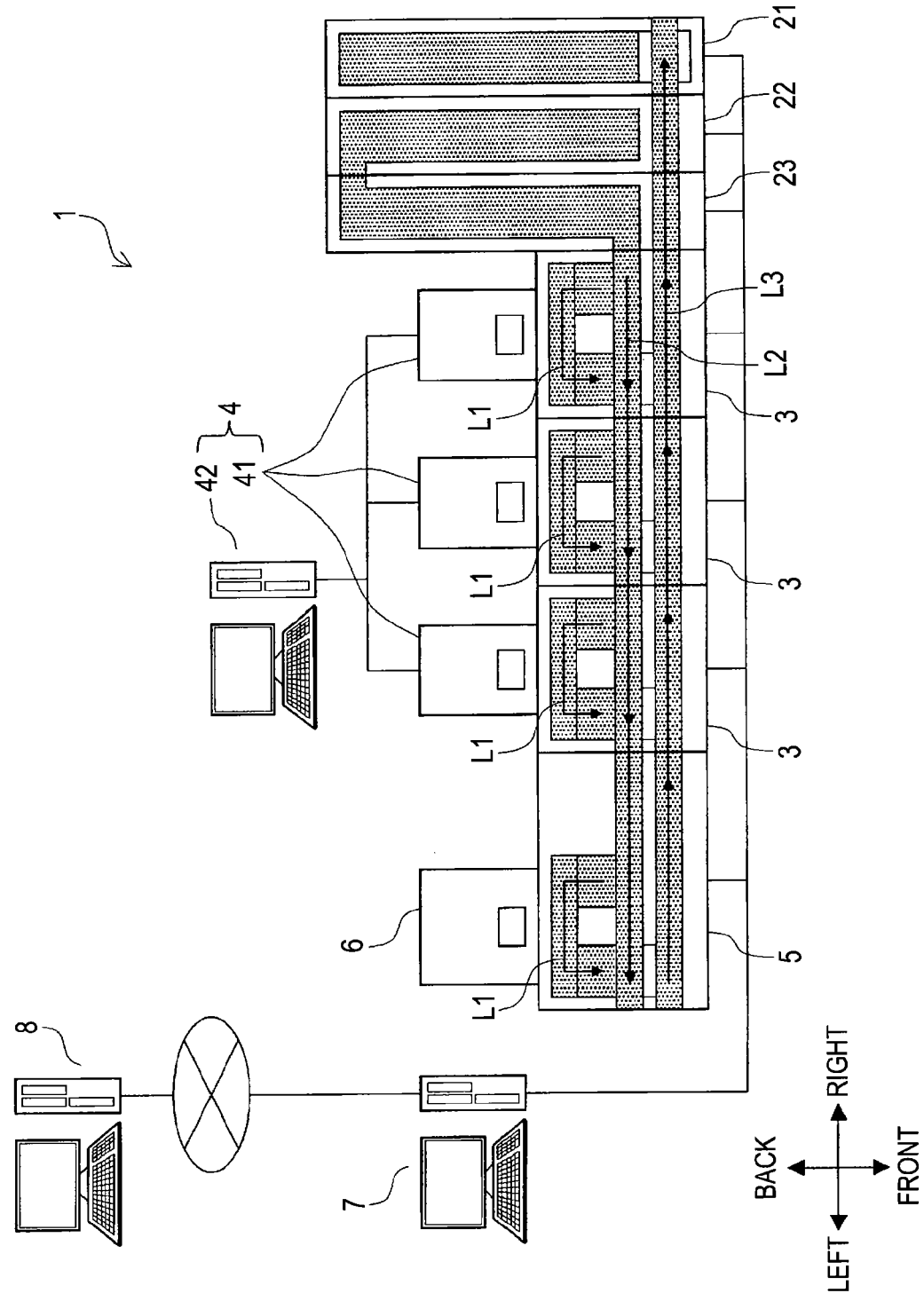
FIG. 1 is a diagram showing the configuration of a sample analysis system according to a first embodiment.

FIG. 1 is a plan view showing the configuration when a sample analysis system 1 is viewed from the upper side. The sample analysis system 1 according to this embodiment is configured to include a sample recovery unit 21, a sample insertion unit 22, a sample output unit 23, three sample transport units 3, a blood cell analysis apparatus 4, a sample transport unit 5, a smear preparation apparatus 6 and a transport controller 7. In addition, the sample analysis system 1 of this embodiment is connected to a host computer 8 via a communication network so as to communicate therewith.

The sample recovery unit 21, the sample insertion unit 22 and the sample transport unit 23 are configured so that a plurality of sample racks can be placed therein.

Figure 2A:
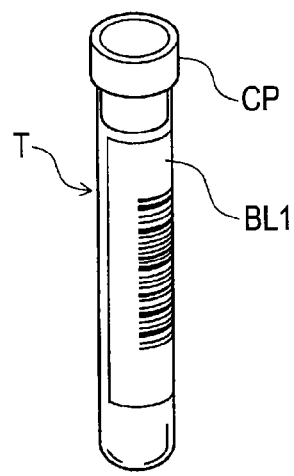
FIGS. 2A and 2B are diagrams showing the configurations of a sample container and a sample rack.
Figure 2B:
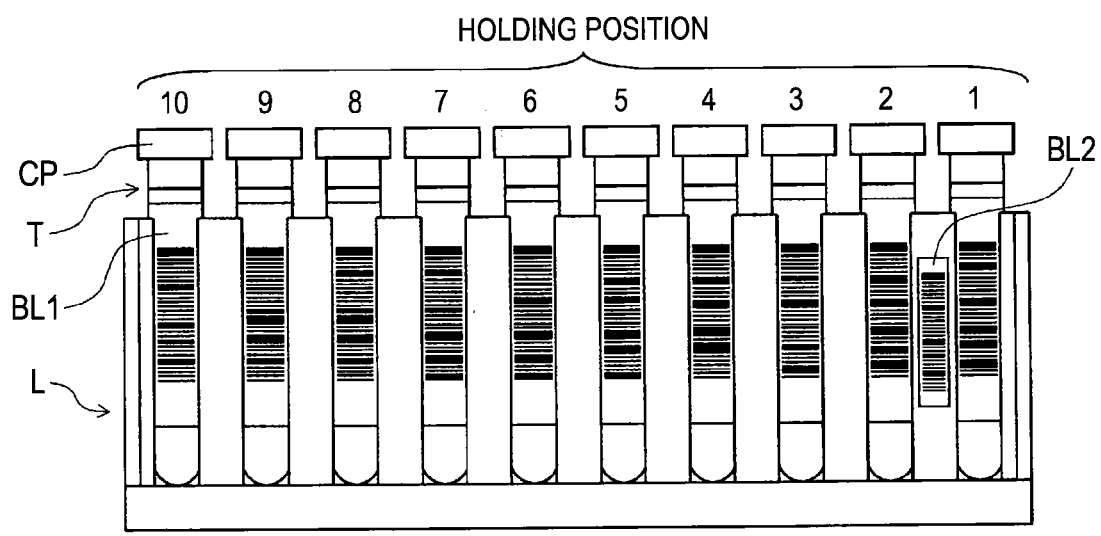

FIG. 2 is a diagram showing the configurations of a sample container T and a sample rack L. FIG. 2A is a perspective view showing the appearance of a sample container T and FIG. 2B is a front view of a sample rack L.

Referring to FIG. 2A, a sample container T is a tubular container made of glass or a synthetic resin having translucency and the upper end thereof is opened. In the sample container, a blood sample collected from a patient is contained and the opening of the upper end is sealed by a cap section CP. A bar-code label BL1 is adhered to a side surface of the sample container T. A bar-code showing a sample ID is printed on the bar-code label BL1.

Referring to FIG. 2B, in a sample rack L, ten holding positions are formed so as to arrange and hold ten sample containers T in a vertical state (erect state). In addition, as shown in the drawing, a bar-code label BL2 is adhered to the front side of the sample rack L. A bar-code showing a rack ID is printed on the bar-code label BL2.

Returning to FIG. 1, the sample recovery unit 21 stores sample racks L in which analysis has ended. The sample insertion unit 22 stores sample racks L which are inserted by an operator, and outputs the stored sample racks L to the sample output unit 23. In addition, the sample recovery unit 21 and the sample insertion unit 22 are connected to the transport controller 7 so as to communicate therewith.

In the sample output unit 23, a rack ID of the sample rack L which is output from the sample insertion unit 22 and a sample ID of the sample container T which is associated with a holding position in the sample rack L are read. The sample output unit 23 outputs to the sample transport unit 3 the sample rack L, the bar-code of which has been read. In addition, the sample output unit 23 is connected to the transport controller 7 so as to communicate therewith, and the rack ID and the sample ID read by the sample output unit 23 are transmitted to the transport controller 7. The configurations of the sample insertion unit 22 and the sample output unit 23 will be described later with reference to FIG. 3.

As shown in the drawing, the three sample transport units 3 are disposed in front of three measuring units 41, respectively. The neighboring two sample transport units 3 are connected to each other so as to deliver sample racks L. The right end of the sample transport unit 3 on the right side is connected to the sample output unit 23 so as to deliver sample racks L, and the left end of the sample transport unit 3 on the left side is connected to the sample transport unit 5 so as to deliver sample racks L. In addition, the three sample transport units 3 are connected to an information processing unit 42 and the transport controller 7 so as to communicate therewith.

As shown in the drawing, in these three sample transport units 3, two transport lines L1 and L2 for transporting sample racks L are set by dividing cases into the case in which the measurement of a sample is performed in the respective corresponding measuring units 41 and the case in which the measurement is not performed. That is, when the measurement of a sample is performed by the measuring unit 41, a sample rack L is transported along the transport line L1 shown by the rear arrow. When the measurement of a sample is not performed by the measuring unit 41, a sample rack L is transported along the transport line L2 shown by the intermediate left-pointing arrow so as to skip the measuring unit 41.

Further, as shown in the drawing, in the three sample transport units 3, a transport line L3 for transporting sample racks L to the sample recovery unit 21 is set. That is, a sample rack L, for which measurement or preparation of a smear has ended, is transported along the transport line L3 shown by the front right-pointing arrow and is recovered by the sample recovery unit 21. The configuration of the sample transport unit 3 will be described later with reference to FIG. 4.

The blood cell analysis apparatus 4 is an optical flow cytometry type multiple blood cell analysis apparatus and includes the three measuring units 41 and the information processing apparatus 42. The information processing unit 42 is connected to the three measuring units 41 so as to communicate therewith, and controls the operations of the three measuring units 41. In addition, the information processing unit 42 is also connected to the three sample transport units 3 so as to communicate therewith.

The three measuring units 41 measure a blood sample which is contained in a sample container T. That is, each of the three measuring units 41 takes the sample container T from the sample rack L at a predetermined position on the transport line L1 of the sample transport unit 3 disposed in front of the measuring unit. The blood sample contained in the sample container T is measured in the measuring unit 41. When the measurement in the measuring unit 41 is completed, the sample container T returns to the original holding position in the sample rack L again. The configuration of the measuring unit 41 will be described later with reference to FIG. 5.

The sample transport unit 5 is disposed in front of the smear preparation apparatus 6. As in the sample transport unit 3, transport lines L1, L2 and L3 are set in the sample transport unit 5. In addition, the sample transport unit 5 is connected to the transport controller 7 so as to communicate therewith. Further, the sample transport unit 5 is connected to the smear preparation apparatus 6, and the smear preparation apparatus 6 is driven in response to an instruction from the sample transport unit 5.

In the smear preparation apparatus 6, a smear of a blood sample is prepared. That is, first, the smear preparation apparatus 6 suctions a blood sample contained in a sample container T at a predetermined position on the transport line L1 of the sample transport unit 5. Next, the suctioned blood sample is dropped onto a glass slide, thinly extended on the glass slide and then is dried. After that, a liquid dye is supplied to the glass slide to dye the blood on the glass slide and a smear is prepared.

Whether the preparation of a smear is required is determined by the transport controller 7 on the basis of the analysis result of the three measuring units 41. As described later, the analysis result of each measuring unit 41 is transmitted to the transport controller 7 via the sample transport unit 3. When the transport controller 7 determines that the preparation of a smear is required, the sample rack L storing a target sample is transported along the transport line L1 of the sample transport unit 5 and a smear is prepared in the smear preparation apparatus 6.

The transport controller 7 is connected to the sample recovery unit 21, the sample insertion unit 22, the sample output unit 23, the three sample transport units 3 and the sample transport unit 5 so as to communicate therewith and controls the driving of each unit. As the transport controller 7, for example, a separate personal computer or a computer incorporated in the system is used.

When receiving the rack ID of a sample rack L, the sample ID of a sample container T and the holding position of the sample container T from the sample output unit 23, the transport controller 7 inquires of the host computer 8 for a measurement order. When receiving the measurement order from the host computer 8, the transport controller 7 stores the measurement order in association with the rack ID, the sample ID and the holding position.

In addition, on the basis of a time interval during which a sample rack L is output to the sample output unit 23 from the sample insertion unit 22, the transport controller 7 decides whether the sample rack L which is output from the sample output unit 23 is transported to any of the three measuring units 41. The transport controller 7 transmits the stored measurement order to the sample transport unit 3 in front of the measuring unit 41 decided as a transport destination. The transport controller 7 controls each sample transport unit 3 so as to transport the sample rack L to the measuring unit 41 decided as the transport destination. Such decision of the transport destination will be described later with reference to FIGS. 9 to 11.

The host computer 8 is connected to the communication network and can communicate with the transport controller 7. In a storage section of the host computer 8, measurement orders are stored. When the transport controller 7 requests a measurement order including a sample ID, the host computer 8 reads out the measurement order corresponding to the sample ID from the storage section and transmits the measurement order to the transport controller 7.

FIG. 3 is a plan view showing the configuration when the sample insertion unit 22 and the sample output unit 23 are viewed from the upper side. In FIG. 3, for the sake of convenience, the transportation of a sample rack L in the right direction along the transport line L3 is omitted in the drawing.

When a sample rack L is inserted onto a transport passage 221 of the sample insertion unit 22, a rack input mechanism 222 moves backward while engaging with the front ends of the sample rack L and thus the sample rack L is sent to the rear position (hereinafter, referred to as "position P1") of the transport passage 221. When the sample rack L1 is positioned at the position P1, a rack output mechanism 223 is driven in the left direction. In this manner, the sample rack L is output to the rear position (hereinafter, referred to as "position P2") of a transport passage 231 of the rack output unit 23 from the position P1. A reflective sensor 232 can detect whether the sample rack L is positioned at the position P2.

A bar-code reading section 233 reads the rack ID of the sample rack L positioned at the position P2 and a sample ID of a sample container T in association with the holding position in the sample rack L. By a rack input mechanism 234, the sample rack L in which the reading of the bar-codes has been completed at the position P2 is sent to a position (hereinafter, referred to as "position P3") which is moved forward by a width in the front-back direction of the sample rack L from the position 2. In this manner, even when a subsequent sample rack L is positioned at the position P1, this sample rack L can be rapidly output to the position P2.

Next, the sample rack L which is positioned at the position P3 is sent toward the forward position (hereinafter, referred to as "position P4") of the transport passage 231 when a rack input mechanism 235 moves forward while engaging with the rear ends of the sample rack L. Here, a contact sensor 236 is disposed on the front wall of the transport passage 231. When there is a plurality of sample racks L in the rear of the position P4 already, the sample rack L which is sent forward by the rack input mechanism 235 is pressed against the rearmost sample rack L among the plurality of sample racks L. Accordingly, the front side surface of the sample rack L which is positioned at the position P4 is pressed against the sensor 236 and it is determined that the delivery of the rack input mechanism 235 is completed. The rack input mechanism 235 which has completed the delivery is returned to the rear of the position at which the delivery has been completed.

The sample rack L which is positioned at the position P4 is output in the left direction (to the sample transport unit 3) by a rack output mechanism 237. At this time, a bar-code reading section 238 reads a bar-code label BL2 of the sample rack L.

In the sample insertion unit 22 and the sample output unit 23, a stepping motor (not shown) is disposed for driving the rack input mechanisms 222, 234 and 235 and the rack output mechanisms 223 and 237. In addition, in the sample insertion unit 22, a sensor (not shown) for detecting the position of a sample rack L on the transport passage 221 is disposed at a corresponding position.

Figure 4:
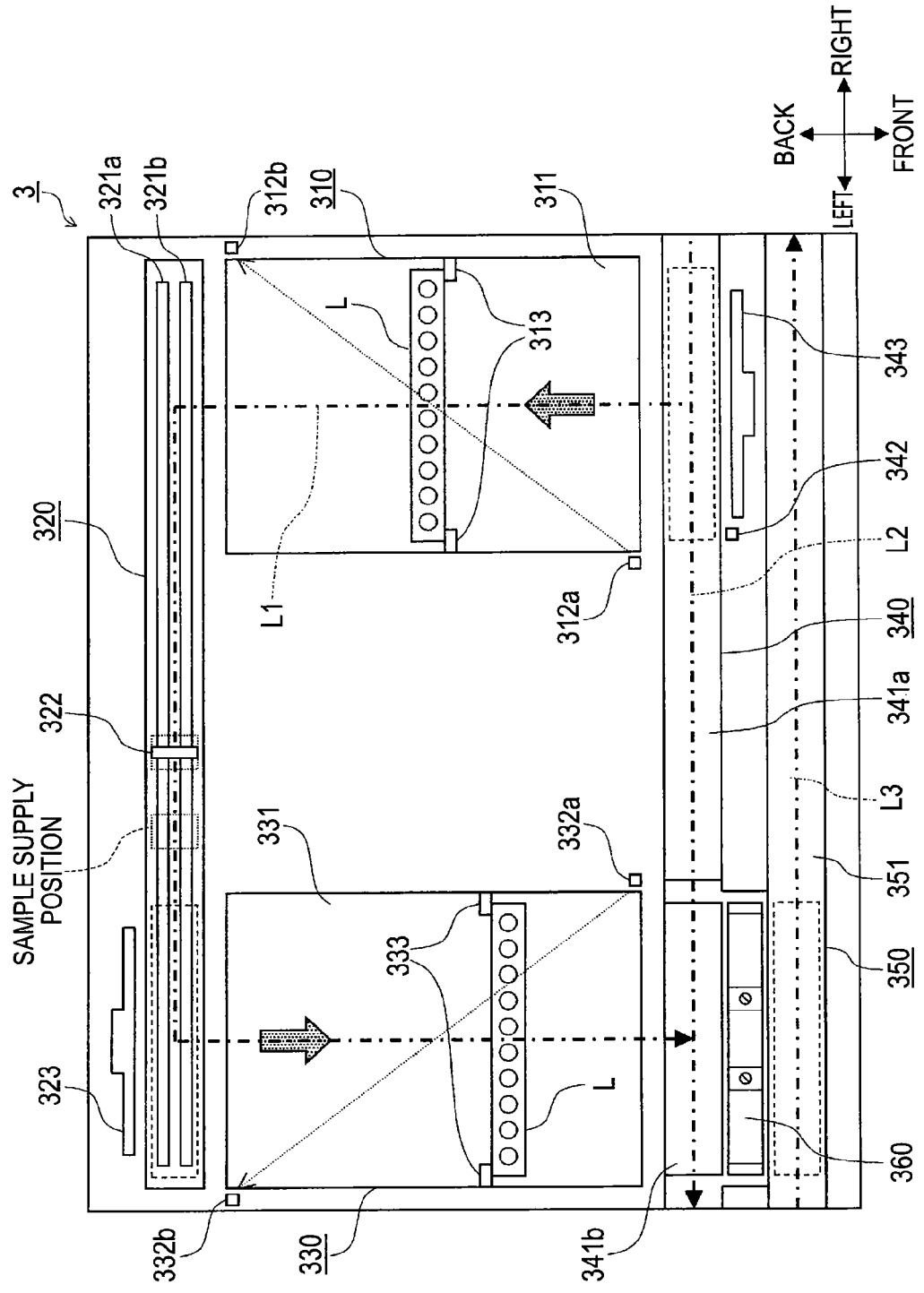
FIG. 4 is a plan view showing the configuration of a sample transport unit according to the first embodiment.

FIG. 4 is a plan view showing the configuration when the sample transport unit 3 is viewed from the upper side. The sample transport unit 3 includes a pre-analysis rack holding section 310, a rack transport section 320, a post-analysis rack holding section 330 and rack transport sections 340 and 350.

When the measurement of a sample rack L is not performed, the sample rack L is linearly sent to the left end from the right end of the rack transport section 340 along the transport line L2 by belts 341*a* and 341*b* of the rack transport section 340.

When the measurement of a sample rack L is performed, the sample rack L is sent to the right end position of the rack transport section 340, which is shown by the broken line in the right lower portion of FIG. 4. That is, a reflective sensor 342 shown in FIG. 4 detects that the sample rack L has been transported to the position shown by the broken line in the right lower portion of FIG. 4. At this timing, the belt 341*a* is stopped. Then, when a rack pushing mechanism 343 moves backward, the sample rack L is pushed to the front end of a transport passage 311 of the pre-analysis rack holding section 310. When optical sensors 312*a* and 312*b* including a light-emitting section and a light-receiving section detect the sample rack L on the transport passage 311, a rack input mechanism 313 moves backward while engaging with the front ends of the sample rack L and the sample rack L is sent to the back. In this manner, when the sample rack L is sent up to the right end position of the rack transport section 320, the belts 321*a* and 321*b* are driven and the sample rack L is sent in the left direction.

After that, the sample rack L arrives at the position of a sample container sensor 322. The sample container sensor 322 is a contact sensor. When a detection target sample container T, which is held in the sample rack L, passes through the position under the sample container sensor 322, the contact piece of the sample container sensor 322 is bent by the sample container T and thus the presence of the sample container T is detected.

At a sample supply position positioned on the left side of the position, at which the sample container T has been detected by the sample container sensor 322, by a distance corresponding to two sample containers, a hand section of the measuring unit 41 which will be described later grips the sample container T and takes the sample container T from the sample rack L. The removed sample container T returns to the sample rack L again after used in the measurement in the measuring unit 41. While the sample container T returns to the sample rack L, the transportation of the sample rack L is on standby.

In this manner, when the measurement of the samples in all of the sample containers T held in the sample rack L is completed, the sample rack L is sent up to the left end position of the rack transport section 320 shown by the broken line in FIG. 4 by the belts 321*a* and 321*b* and the driving of the belts 321*a* and 321*b* is stopped. Then, the sample rack L is sent to the rear end of a transport passage 331 of the post-analysis rack holding section 330 by a rack pushing mechanism 323. When optical sensors 332*a* and 332*b* including a light-emitting section and a light-receiving section detect the sample rack L on the transport passage 331, a rack input mechanism 333 moves forward while engaging with the rear ends of the sample rack L and the sample rack L is sent to the front. At this time, a partition section 360 which is in front of the post-analysis rack holding section 330 and is between the rack transport sections 340 and 350 is controlled to be opened and closed and the sample rack L is positioned in either of the rack transport sections 340 or 350.

As a result of the measurement by the measuring unit 41, when it is determined that the smear preparation apparatus 6 on the downstream side needs to prepare smears related to sample containers T which are held in the sample rack L, the sample rack L moves up to the left end position of the rack transport section 340 by the rack input mechanism 333 in a state in which the rack transport sections 340 and 350 are partitioned by the partition section 360. Then, the sample rack L is output to the sample transport unit on the downstream side by the belt 341*b* of the rack transport section 340.

On the other hand, as a result of the measurement by the measuring unit 41, when it is determined that the smear preparation apparatus 6 on the downstream side does not need to prepare smears related to the sample containers T which are held in the sample rack L, the upper side of the partition section 360 is dropped to be disposed at the same height as the upper side of the belt 341*b* of the rack transport section 340 and the sample rack L is moved up to the left end position of the rack transport section 350 by the rack input mechanism 333. In this manner, by the rack input mechanism 333, the sample rack L is moved across the rack transport section 340 from the post-analysis rack holding section 330 up to the left end position of the rack transport section 350, which is shown by the broken line in the left lower portion of the same drawing. Then, the sample rack L is moved in the right direction along the transport line L3 by a belt 351 of the rack transport section 350. In this manner, the sample rack L which is transported along the transport line L3 is stored in the sample recovery unit 21.

In the sample transport unit 3, a stepping motor (not shown) for driving the rack pushing mechanisms 343 and 323, the rack input mechanisms 313 and 333, the belts 321*a*, 321*b*, 341*a*, 341*b* and 351 and the partition section 360 is disposed. In addition, in the sample transport unit 3, in addition to the sensors 342, 312*a*, 312*b*, 332*a* and 332*b* and the sample container sensor 322, a sensor (not shown) for detecting the position of a sample rack L on the transport passage is disposed at a corresponding position.

Figure 5:
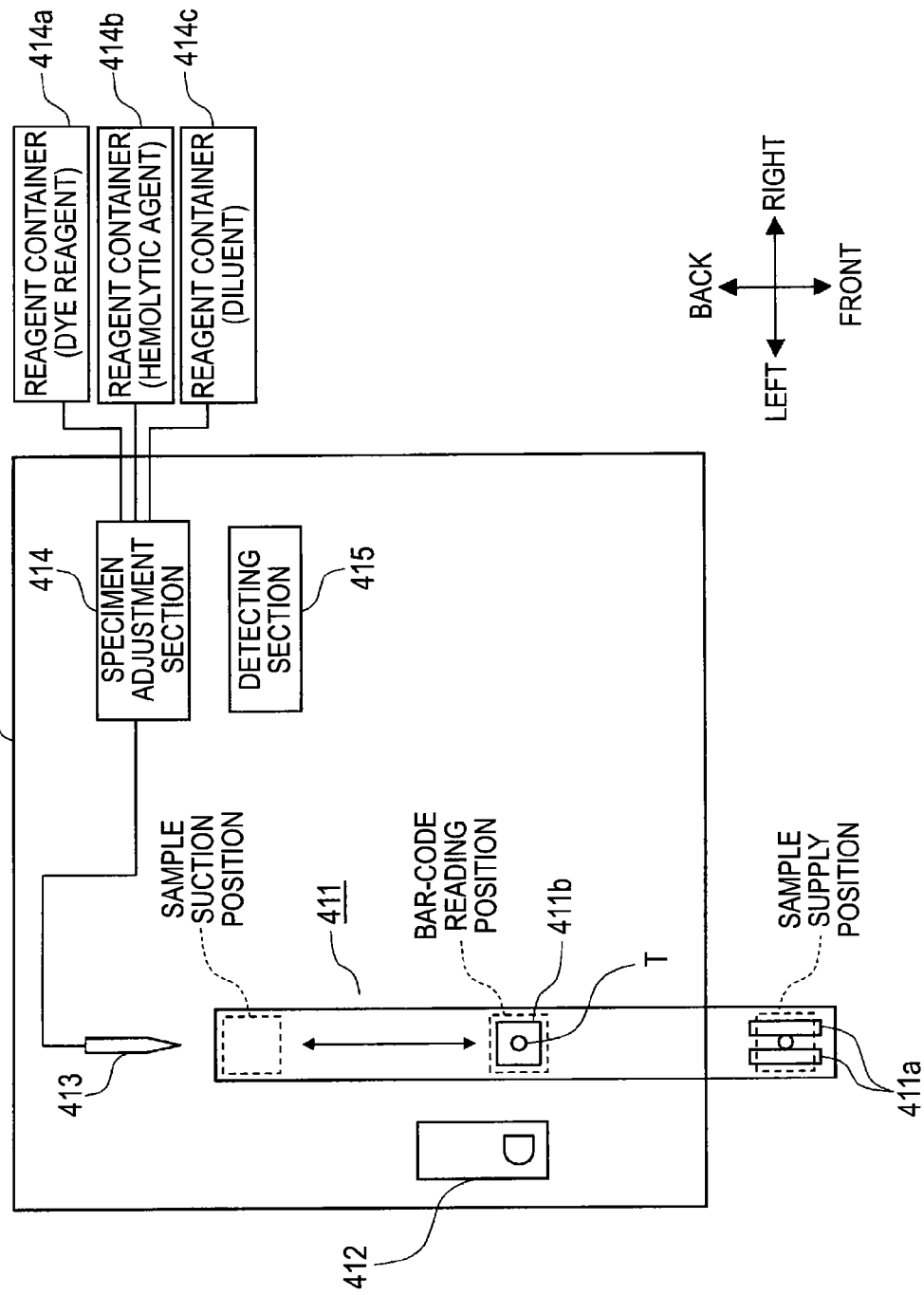
FIG. 5 is a schematic diagram showing the configuration of a measuring unit according to the first embodiment.

FIG. 5 is a schematic diagram showing the configuration when the measuring unit 41 is viewed from the upper side. The measuring unit 41 includes a sample container transport section 411, a bar-code reading section 412, a sample suction section 413, a specimen adjustment section 414 and a detecting section 415.

The sample container transport section 411 includes a hand section 411*a* and a sample container setting section 411*b*. The hand section 411*a* grips a sample container T positioned at the sample supply position and takes the sample container T upward from the sample rack L. The removed sample container T is stirred by the hand section 411*a* and then set in the sample container setting section 411*b*. Regarding the sample container T which is set in the sample container setting section 411*b*, the bar-code reading section 412 reads a bar-code label BL1 adhered to the sample container T at a bar-code reading position. Then, when the sample container setting section 411*b* is moved backward, the sample container T is positioned at the sample suction position under the sample suction section 413. The sample suction section 413 suctions the sample in the sample container T which is positioned at the sample suction position. After that, the sample container T returns to the original holding position in the original sample rack L along the original path.

The specimen adjustment section 414 includes a plurality of reaction chambers (not shown). The specimen adjustment section 414 is connected to reagent containers 414a to 414c and can supply a dye reagent of the reagent container 414a, a hemolytic agent of the reagent container 414b and a diluent of the reagent container 414c to the reaction chambers. In addition, the specimen adjustment section 414 is also connected to the sample suction section 413 and can supply the blood sample which is suctioned by the sample suction section 413 to the reaction chambers. Further, the specimen adjustment section 414 mixes and stirs the sample and the reagent together in the reaction chamber and prepares a specimen for measurement of the detecting section 415.

The detecting section 415 measures a specimen which is prepared by the specimen adjustment section 414. The measurement data which is obtained by such measurement is analyzed by the information processing unit 42.

Figure 6:
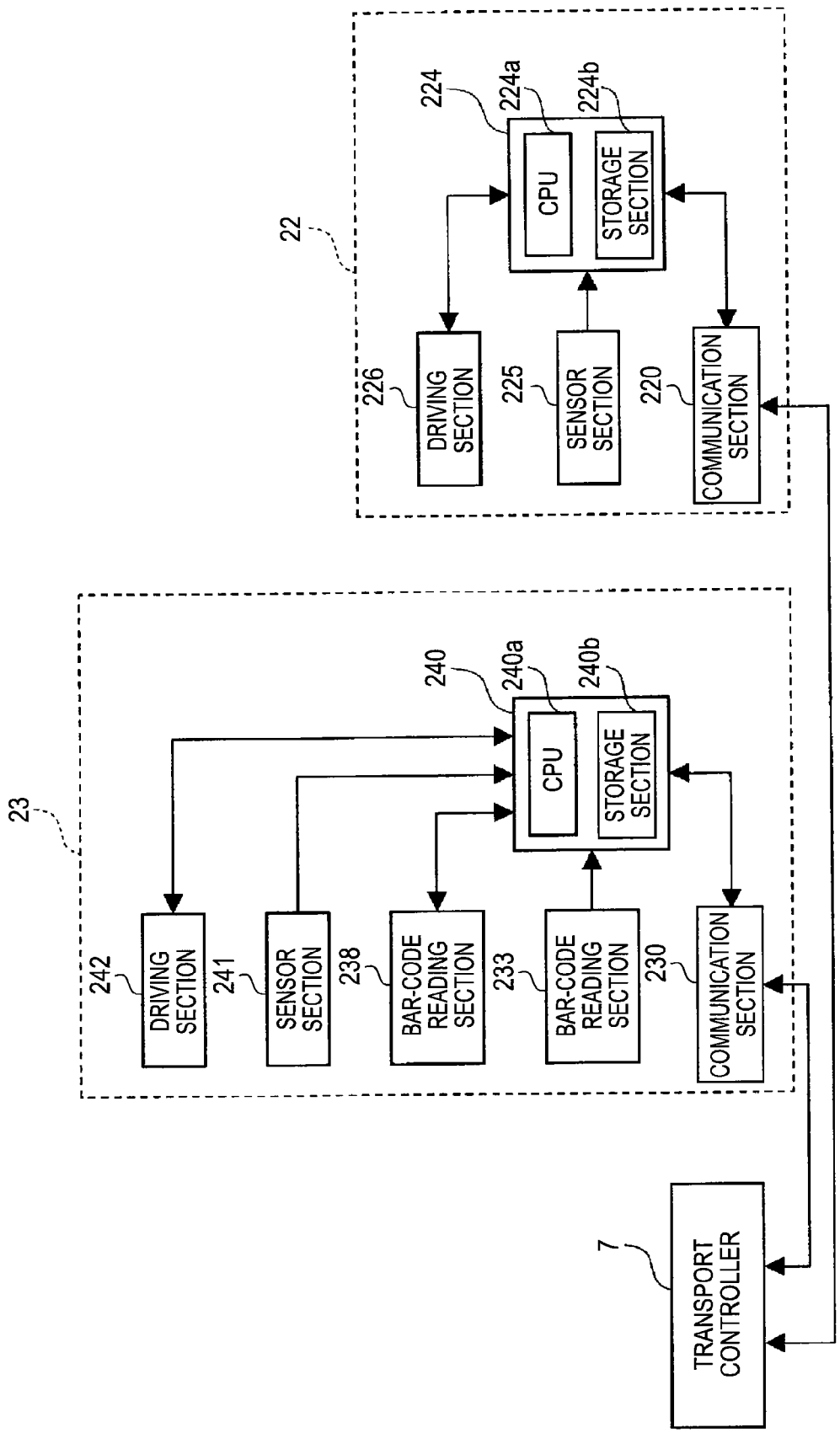
FIG. 6 is a diagram showing the outline of the circuit configurations of the sample insertion unit and the sample output unit according to the first embodiment.

FIG. 6 is a diagram showing the outline of the circuit configurations of the sample insertion unit 22 and the sample output unit 23.

The sample insertion unit 22 includes a communication section 220, a control section 224, a sensor section 225 and a driving section 226. The communication section 220 performs data communication with the transport controller 7. The control section 224 includes a CPU 224a and a storage section 224b. The CPU 224a executes computer programs which are stored in the storage section 224b and controls the sections in accordance with the control section of the transport controller 7. The storage section 224b includes storage means such as a ROM, a RAM and a hard disk.

The sensor section 225 includes a sensor for detecting the position of a sample rack L on the transport passage 221. The driving section 226 includes the above-described rack input mechanism 222, rack output mechanism 223 and a stepping motor which drives these mechanisms.

The sample output unit 23 includes a communication section 230, the bar-code reading sections 233 and 238, a control section 240, a sensor section 241 and a driving section 242. The communication section 230 performs data communication with the transport controller 7. The control section 240 includes a CPU 240a and a storage section 240b. The CPU 240a executes computer programs which are stored in the storage section 240b and controls the sections in accordance with the control section of the transport controller 7. The storage section 240b includes storage means such as a ROM, a RAM and a hard disk.

The rack ID of a sample rack L which is read by the bar-code reading section 233 and the sample ID of a sample container T which is associated with the holding position in the sample rack L are transmitted to the transport controller 7 via the control section 240. In addition, the rack ID of a sample rack L which is read by the bar-code reading section 238 is also transmitted to the transport controller 7 via the control section 240.

The sensor section 241 includes the above-described sensors 232 and 236 and a detection signal of the sensor section 241 is output to the control section 240. The driving section 242 includes the above-described rack input mechanisms 234 and 235, rack output mechanism 237 and a stepping motor which drives these mechanisms.

Figure 7:
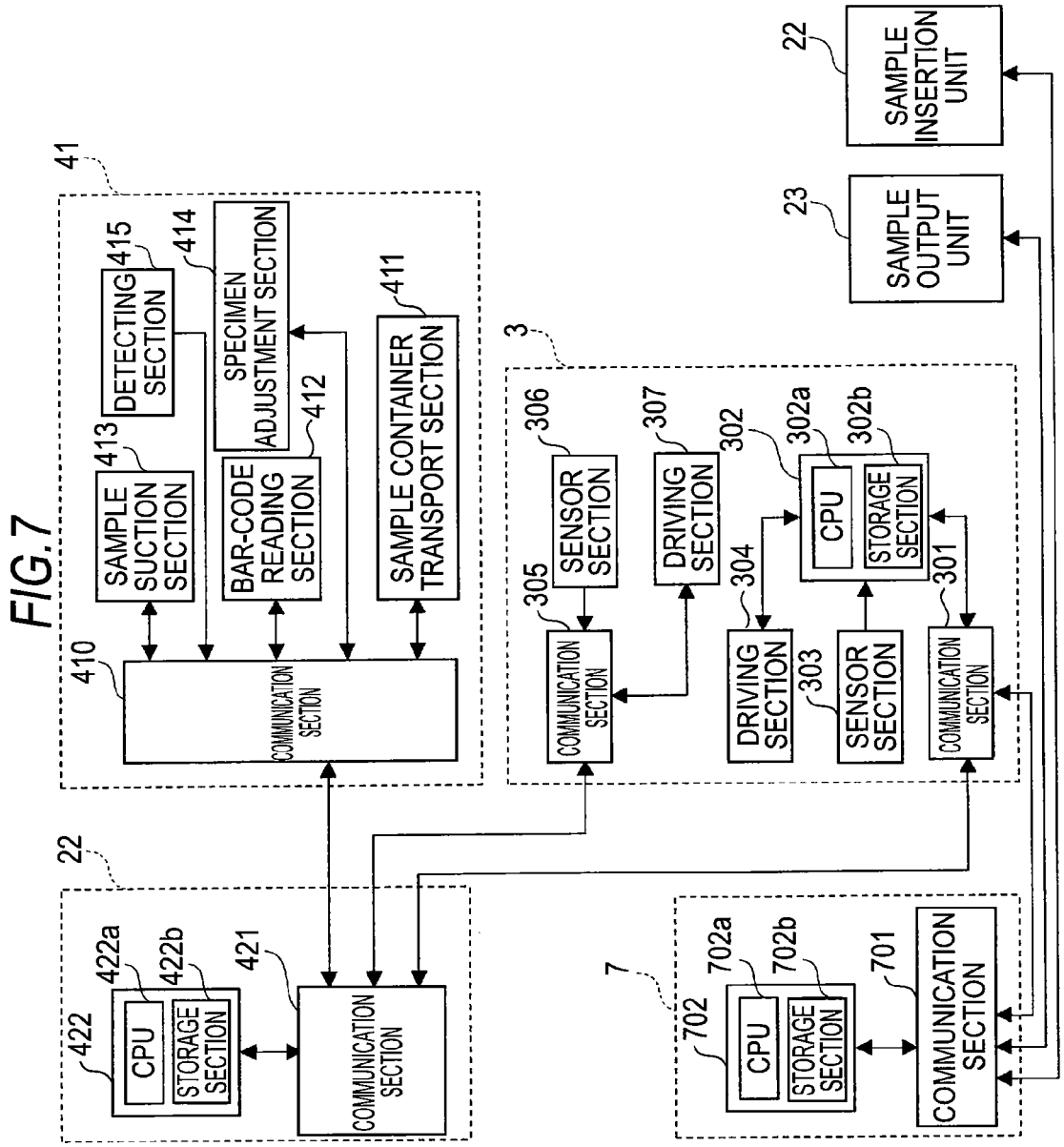
FIG. 7 is a diagram showing the outline of the circuit configurations of the sample transport unit, the measuring unit, an information processing unit and a transport controller according to the first embodiment.

FIG. 7 is a diagram showing the outline of the circuit configurations of the sample transport unit 3, the measuring unit 41, the information processing unit 42 and the transport controller 7. In the same drawing, for the sake of convenience, only one sample transport unit 3 and one measuring unit 41 are shown, but the other sample transport units 3 and measuring units 41 also have the same configuration.

The sample transport unit 3 includes communication sections 301 and 305, a control section 302, sensor sections 303 and 306 and driving sections 304 and 307.

The driving section 307 performs the transportation of a sample rack L in a zone from when the sample rack L is forced into the pre-analysis rack holding section 310 to when the sample rack L is pushed to the post-analysis rack holding section 330. Sensors which are disposed in this zone are included in the sensor section 306 and the output of these sensors is supplied to the information processing unit 42. In addition, the driving section 304 performs the transportation of a sample rack L in a zone other than the transport zone of the driving section 307. Sensors which are disposed in this zone are included in the sensor section 303 and the output of these sensors is supplied to the transport controller 7.

The communication section 301 performs data communication between the transport controller 7 and the information processing unit 42. The control section 302 includes a CPU 302a and a storage section 302b. The CPU 302a executes computer programs which are stored in the storage section 302b and controls the driving section 304 in accordance with a control section 702a of the transport controller 7. The storage section 302b includes storage means such as a ROM and a RAM. The storage section 302b stores the number of measurements which has been performed by the measuring unit 41 corresponding to the present sample transport unit 3. In addition, the storage section 302b is also used as a work area of the CPU 302a.

Here, the number of measurements which is stored in the storage section 302b will be described.

FIG. 8A is a diagram showing the number of measurements of the measuring unit 41, which is stored in the storage section 302b of the sample transport unit 3. In FIG. 8A, sample transport units (1) to (3) indicate the left, central and right sample transport units 3 among the three sample transport units 3.

As shown in the drawing, in the storage sections 302b of the sample transport units (1) to (3), N1, N2 and N3 are stored respectively as the number of measurements of the corresponding measuring unit 41. This number of measurements is updated at the timing when the measurement of a sample is completed by the corresponding measuring unit 41. That is, when the measurement of a sample is completed by the measuring unit 41 and the measurement result of the sample is received, the information processing unit 42 issues a notice to the corresponding sample transport unit 3. When receiving the notice, the CPU 302a of the sample transport unit 3 adds 1 to the number of measurements which is stored in the storage section 302b.

Returning to FIG. 7, the sensor section 303 includes the above-described sensors 342, 332a and 332b and a detection signal of the sensor section 303 is output to the control section 302. The driving section 304 includes a lifting and lowering mechanism which lifts and lowers the above-described rack pushing mechanism 343, rack input mechanism 333, belts 341a, 341b and 351 and partition section 360, and a stepping motor which drives these mechanisms.

The communication section 305 performs data communication with the information processing unit 42. The sensor section 306 includes the above-described sensors 312a and 312b and sample container sensor 322, and a detection signal of the sensor section 306 is transmitted to the information processing unit 42 via the communication section 305. The driving section 307 includes the rack pushing mechanism 323, the rack input mechanism 313, the belts 321*a* and 321*b* and a stepping motor which drives these mechanisms. A control section 422 of the information processing unit 42 directly controls each of the sections of the driving section 307.

When detection signals of the sensors 312*a* and 312*b* of the sensor section 306 are transmitted to the information processing unit 42, the information processing unit 42 transmits the detection signals to the control section 302 via the communication section 301 of the corresponding sample transport unit 3. Accordingly, when the CPU 702*a* of the transport controller 7 inquires of each sample transport unit 3 for whether there is the detection by the sensors 312*a* and 312*b*, the control section 302 of each of the sample transport unit 3 transmits whether there is the detection by the sensors 312*a* and 312*b* to the transport controller 7 on the basis of the detection signals transmitted from the information processing unit 42.

The measuring unit 41 includes a communication section 410, the sample container transport section 411, the bar-code reading section 412, the sample suction section 413, the specimen adjustment section 414 and the detecting section 415. The control section 422 of the information processing unit 42 directly controls each of the sections of the measuring unit 41.

The information processing unit 42 includes a communication section 421 and a control section 422. In addition, the information processing unit 42 includes an interface for performing video output, an interface for performing an input operation from a keyboard or the like and a read-out device such as a CD drive or a DVD drive. However, here, the description thereof will be omitted.

The communication section 421 performs data communication between the communication sections 301 and 305 of the sample transport unit 3 and the communication section 410 of the measuring unit 41. The control section 422 includes a CPU 422*a* and a storage section 422*b*. The CPU 422*a* executes computer programs which are stored in the storage section 422*b*. The storage section 422*b* includes storage means such as a ROM, a RAM and a hard disk.

The CPU 422*a* analyzes the blood on the basis of the measurement result (particle data) received from the measuring unit 41 and displays the analysis result on a display section (not shown). In addition, the CPU 422*a* transmits the analysis result to the transport controller 7 via the sample transport unit 3.

The transport controller 7 includes a communication section 701 and a control section 702. In addition, the transport controller 7 includes an interface for performing video output, an interface for performing an input operation from a keyboard or the like and a read-out device such as a CD drive or a DVD drive.

The communication section 701 performs data communication among the sample insertion unit 22, the sample output unit 23 and the three sample transport units 3. The control section 702 includes a CPU 702*a* and a storage section 702*b*. The CPU 702*a* executes computer programs which are stored in the storage section 702*b*. The storage section 702*b* includes storage means such as a ROM, a RAM and a hard disk.

The CPU 702*a* controls the driving of the sample insertion unit 22, the sample output unit 23 and the three sample transport units 3 in accordance with a computer program. In addition, the CPU 702*a* receives the number of measurements of each measuring unit 41 from the storage section 302*b* of the corresponding sample transport unit 3. The received number of measurements of each measuring unit 41 is stored for each measuring unit 41 in the storage section 702*b*.

In addition, the CPU 702*a* controls the driving section 226 of the sample insertion unit 22 and the driving section 242 of the sample output unit 23 on the basis of detection signals from the sensor section 225 of the sample insertion unit 22 and the sensor section 241 of the sample output unit 23. The CPU 702*a* controls the driving section 304 of the sample transport unit 3 on the basis of a detection signal from the sensor section 303 of the sample transport unit 3. The CPU 702*a* determines whether the preparation of a smear is required on the basis of the sample analysis result received from the information processing unit 42 via the sample transport unit 3.

The sample transport unit 5 (not shown) has the same configuration as the sample transport unit 3. The sample transport unit 5 controls a driving section of the sample transport unit 5 in accordance with an instruction of the transport controller 7, and the smear preparation apparatus 6 (not shown) is driven in response to an instruction of the sample transport unit 5.

FIGS. 9 to 12 are flowcharts showing that a sample rack L which is positioned at the position P1 of FIG. 3 is controlled to be output toward the sample transport unit 3.

The CPU 702*a* of the transport controller 7 performs the following control operation. In addition, P2 to P4 flags, which are used in the following flowcharts, show whether a sample rack L is positioned at the positions P2 to P4 of FIG. 3, respectively. That is, the case in which values of the P2 to P4 flags are 0 show that the sample rack L is not positioned at the positions P2 to P4, and the case in which values of the P2 to P4 flags are 1 show that the sample rack L is positioned at the positions P2 to P4. The initial values of the P2 to P4 flags are 0, and the P2 to P4 flags are stored in the storage section 702*b* of the transport controller 7.

Figure 9B:
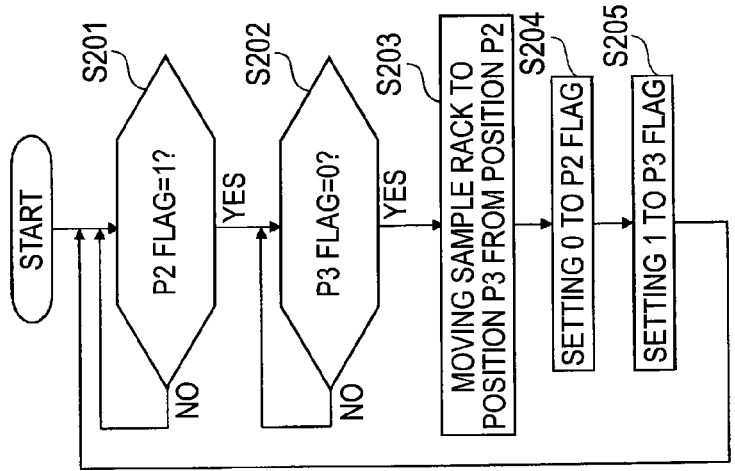
FIGS. 9A and 9B are flowcharts showing that a sample rack which is positioned at the rear position of the sample insertion unit according to the first embodiment is controlled to be output toward the sample transport unit.
Figure 9A:
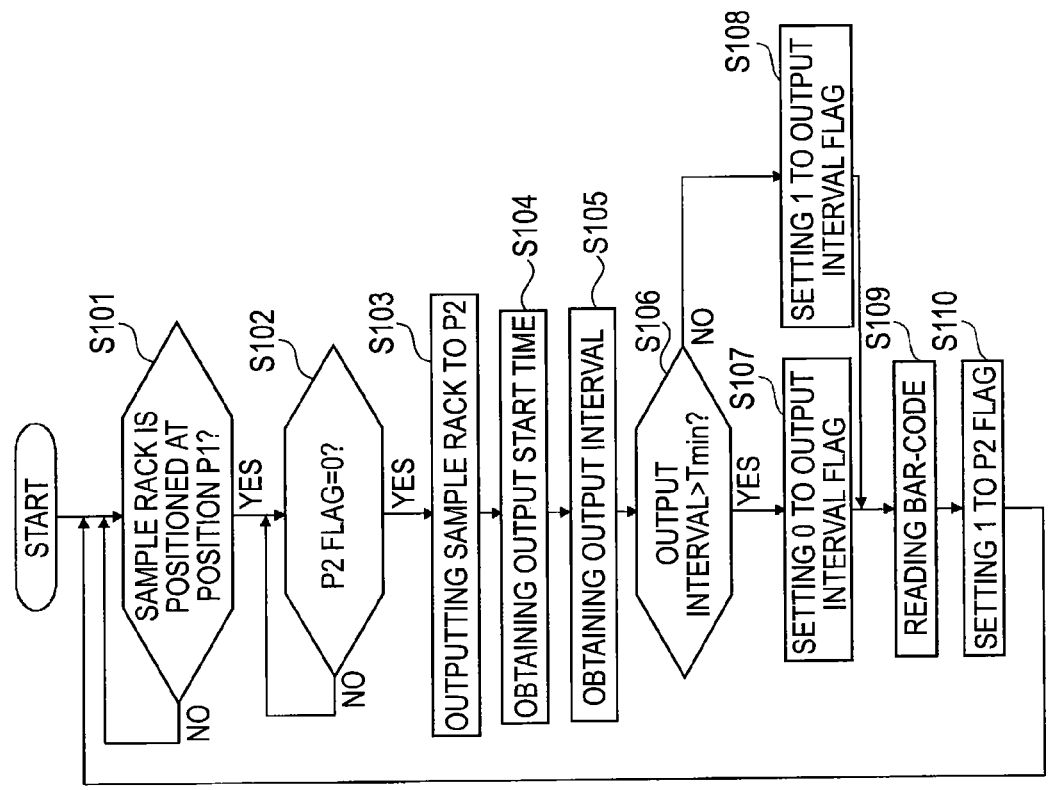

FIG. 9A is a flowchart showing that a sample rack L which is positioned at the position P1 is controlled to be output to the position P2.

When it is determined that a sample rack L is positioned at the position P1 (S101: YES) and when it is determined that a value of the P2 flag is 0 (S102: YES), the CPU 702*a* of the transport controller 7 outputs the sample rack L positioned at the position P1 to the position P2 by driving the rack output mechanism 223 (S103). At this time, the CPU 702*a* obtains a time when the output of the sample rack L toward the position P2 from the position P1 is started (S104) and stores it in the storage section 702*b*.

Next, the CPU 702*a* obtains a difference (hereinafter, referred to as "output interval") between the time obtained at this time in S104 and a time when the output of a directly previous sample rack L toward the position P2 from the position P1 is started (S105), and determines whether this output interval is greater than Tmin (S106). Here, Tmin indicates an output interval when there is no sample rack L on the transport passage 231 of the sample output unit 23, sample racks L are continuously output toward the position P2 from the position P1. That is, Tmin is a value when the output interval is minimum.

When it is determined that the output interval is greater than Tmin (S106: YES), 0 is set to the output interval flag (S107). When it is determined that the output interval is not greater than Tmin, that is, when it is determined that the output interval is equal to Tmin (S106: NO), 1 is set to the output interval flag. The output interval flag is stored in the storage section 702*b* of the transport controller 7 and the initial value thereof is 0. When a directly previous sample rack L does not exist, that is, when the sample rack L output at this time is a sample rack L which is initially output, the determination result is YES in S106.

Here, as a state in which the output interval is greater than Tmin, a case in which a time interval during which a sample rack L is inserted into the sample insertion unit 22 is long, or a case in which the moving of a sample rack L on the transport passage 231 of the sample output unit 23 is interrupted and a waiting time is generated for a sample rack L which is to be output toward the position P2 from the position P1 is exemplified.

Next, at the position P2, the bar-code reading section 233 reads a rack ID of the sample rack L and a sample ID of the sample container T which is associated with a holding position in the sample rack L (S109) and 1 is set to the P2 flag (S110). When the process of S109 is completed, the process returns to S101.

FIG. 9B is a flowchart showing that a sample rack L which is positioned at the position P2 is controlled to be sent to the position P3.

When it is determined that a value of the P2 flag is 1 (S201: YES) and when it is determined that a value of the P3 flag is 0 (S202: YES), the CPU 702a of the transport controller 7 moves a sample rack L, which is positioned at the position P2, to the position P3 by driving the rack input mechanism 234 (S203). Further, the CPU 702a sets 0 to the P2 flag (S204) and sets 1 to the P3 flag (S205). When the process of S205 is completed, the process returns to S201.

FIG. 10 is a flowchart showing that a sample rack L which is positioned at the position P3 is controlled to be sent in the direction of the position P4.

When it is determined that the P3 flag is 1 (S301: YES) and when it is determined that a value of the P4 flag is 0 (S302: YES), the CPU 702a of the transport controller 7 moves a sample rack L, which is positioned at the position P3, in the direction of the position P4 by driving the rack input mechanism 235 (S303). At this time, 0 is set to the P3 flag (S304).

In the case in which by moving the sample rack L in the direction of the position P4, as described above, the sensor 236 detects that the front side surface of the sample rack L positioned at the position P4 has been brought into contact with the sensor 236 (S305: YES), 1 is set to the P4 flag (S306). In this manner, the sample rack L which is sent forward is positioned at the position P4 when there are no sample racks L between the sample rack L and the position P4, and in addition, the sample rack L is positioned behind the rearmost sample rack L when there are one or more sample racks L between the sample rack L and the position P4.

Next, the moving of the rack input mechanism 235, which has completed the delivery of the sample rack L, backward is started so as to return to the position P3 (S307). At this time, the number of pulses which are applied to the stepping motor driving the rack input mechanism 235 is counted (S308). When it is determined that the moving of the rack input mechanism 235 to the position P3 has been completed (S309: YES), it is determined whether the counted number of pulses is equal to or less than Pc (S310). Pc is set to the number of pulses which are counted when the rack input mechanism returns to P3 from a predetermined position between the position P3 and the position P4.

Here, the case in which the counted number of pulses is equal to or less than Pc (S310: YES) shows that there is a plurality of sample racks L behind the position P4 on the transport passage 231 and the rearmost sample rack L is positioned nearer to the position P3 than the predetermined position between the position P3 and the position P4. On the other hand, the case in which the counted number of pulses is greater than Pc (S310: NO) shows that even when there is a plurality of sample racks L behind the position P4 on the transport passage 231, the rearmost sample rack L is positioned nearer to the position P4 than the predetermined position between the position P3 and the position P4. That is, when it is determined whether the counted number of pulses is equal to or less than Pc, the extent of the number of sample racks L which are arranged on the transport passage 231 is found.

When it is determined that the counted number of pulses is equal to or less than Pc (P310: YES), 1 is set to a fullness flag (S311) to show that the number of sample racks L which are arranged behind the position P4 is equal to or greater than a predetermined number. On the other hand, when it is determined that the counted number of pulses is greater than Pc (P310: NO), 0 is set to the fullness flag (S312) to show that the number of sample racks L which are arranged behind the position P4 is less than a predetermined number. The fullness flag is stored in the storage section 702b of the transport controller 7 and the initial value thereof is 0. When the process of S311 or S312 is completed, the process returns to A301.

Figure 11:
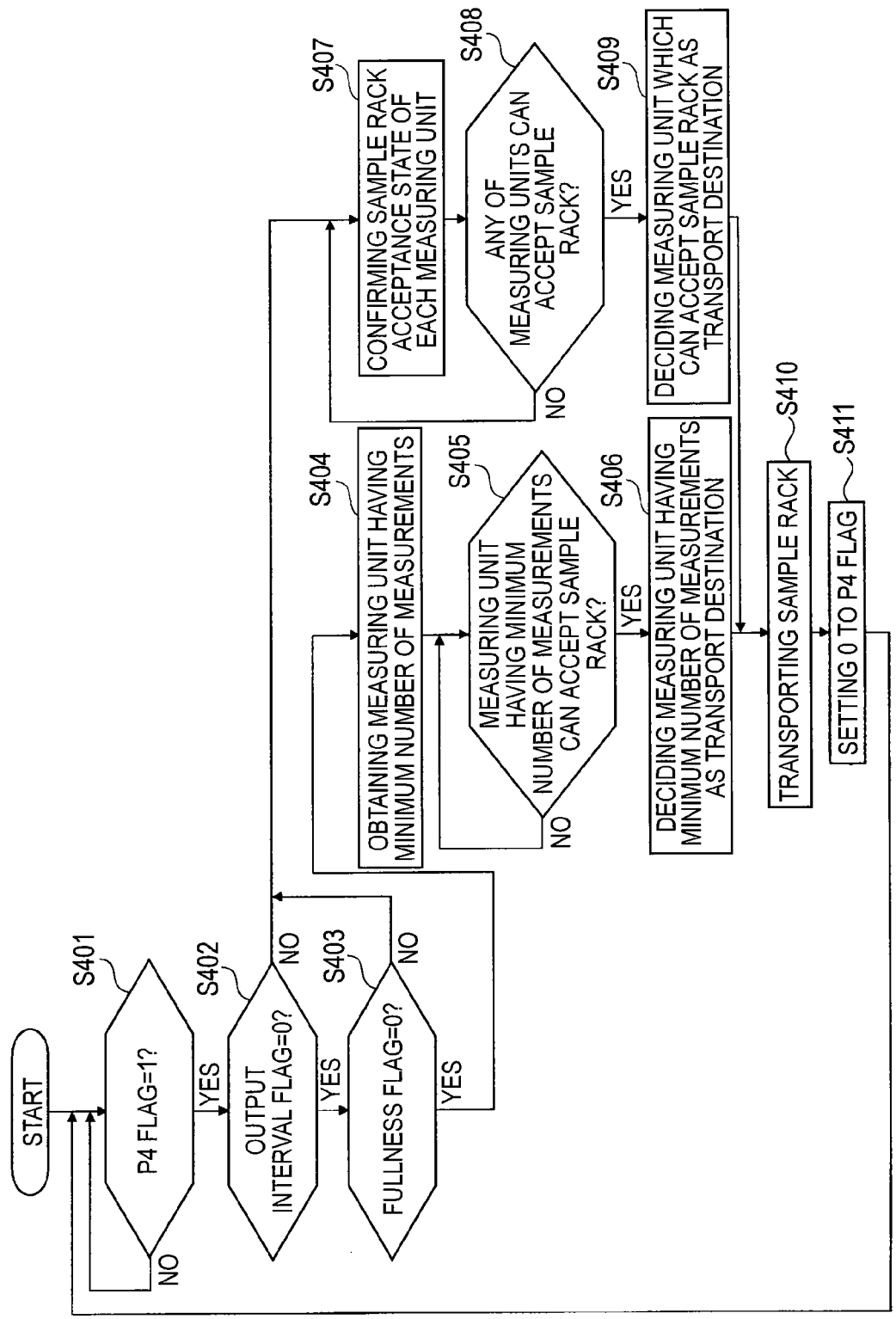
FIG. 11 is a flowchart showing that a sample rack which is positioned at the rear position of the sample insertion unit according to the first embodiment is controlled to be output toward the sample transport unit.

FIG. 11 is a flowchart showing that a sample rack L which is positioned at the position P4 is controlled to be output toward the sample transport unit 3.

When it is determined that the P4 flag is 1 (S401: YES), the CPU 702a of the transport controller 7 determines whether an output interval flag is 0 (S402). When it is determined that the output interval flag is 0 (S402: YES), the CPU 702a determines whether the fullness flag is 0 (S403).

When it is determined that the fullness flag is 0 (S403: YES), the CPU 702a obtains the measuring unit 41 having the minimum number of measurements on the basis of the numbers of measurements which are stored in the memory 702b shown in FIG. 7 (S404). Next, the CPU 702a determines whether the measuring unit 41 having the minimum number of measurements, which is obtained in S404, can accept a sample rack L (S405). In this embodiment, when there are no sample racks L in the pre-analysis rack holding section 310 of the sample transport unit 3 corresponding to the measuring unit 41, it is determined that this measuring unit 41 can accept a sample rack L. In addition, as described above, such confirmation is carried out when the CPU 702a inquires of each sample transport unit 3 for whether there is the detection by the sensors 312a and 312b.

When it is determined that the measuring unit 41 having the minimum number of measurements cannot accept a sample rack L (S405: NO), the process stands by until it is determined that the measuring unit 41 can accept a sample rack L. When it is determined that the measuring unit 41 having the minimum number of measurements can accept a sample rack L (S405: YES), the CPU 702a decides this measuring unit 41 as a transport destination (S406). In addition, when the measuring units 41 having the same number of measurements can accept a sample rack L, the measuring unit 41 on the downstream side (left side) among the measuring units 41 is decided as a transport destination.

On the other hand, when it is determined that the output interval flag is not 0 (S402: NO) or when it is determined that the fullness flag is not 0 (S403: NO), the CPU 702a confirms an acceptance state of a sample rack L for each measuring unit 41 (S407). When it is determined that all the measuring units 41 cannot accept a sample rack L (S408: NO), the process returns to S407. When it is determined that any of the measuring units 41 can accept a sample rack L (S408: YES), the CPU 702a decides as a transport destination the measuring unit 41 which is confirmed as being capable of accepting a sample rack L in S407 (S409). In addition, when the number of the measuring units 41 which can accept a sample rack L is more than one, the measuring unit 41 on the downstream side (left side) among the measuring units 41 is decided as a transport destination.

Next, the CPU 702a transports a sample rack L to the measuring unit 41 which is determined as a transport destination in S406 or S409 (S410). That is, first, a sample rack L which is positioned at the position P4 is output in the left direction from the sample output unit 23 by the rack output mechanism 237. In addition, in order to perform the measurement by the measuring unit 41 which is determined as a transport destination in S406 or S409, the sample rack L is transported to the pre-analysis rack holding section 310 of the sample transport unit 3 corresponding to this measuring unit 41.

Next, the CPU 702a sets 0 to the P4 flag (S411). When the process of S411 is completed, the process returns to S401.

As described above, according to this embodiment, when the output interval is greater than Tmin and the number of sample racks L which are behind the position P4 of the sample output unit 23 is less than a predetermined number, the sample racks L which are measurement targets are determined not to be crowded, and a sample rack L which is output from the sample output unit 23 is transported to the measuring unit 41 having a low measurement load, that is, to the measuring unit 41 having the minimum number of measurements. In this manner, since the three measuring units 41 have almost the same number of measurements, the measurement loads on the measuring units 41 can be equalized. Accordingly, since components and the like of the measuring units 41 are consumed at the same degree, maintenance of the measuring units 41 can be performed around the same time, so the workload for maintenance can be reduced.

In addition, according to this embodiment, in addition to the case in which the output interval is equal to Tmin, when the output interval is greater than Tmin and there is a predetermined number or more of sample racks L behind the position P4 of the sample output unit 23, the sample racks L which are measurement targets are determined to be crowded, and a sample rack L which is output from the sample output unit 23 is transported to the measuring unit 41 which is determined to be capable of accepting a sample rack L. Accordingly, even when the sample analysis system 1 receives a number of sample racks L, the sample measurement process is conducted smoothly.

2. Second Embodiment

In the above-described first embodiment, the measuring unit which transports a sample rack L is decided on the basis of the output interval flag and the fullness flag. However, in this embodiment, statistics on a crowded state of sample racks L are further considered.

Figure 12:
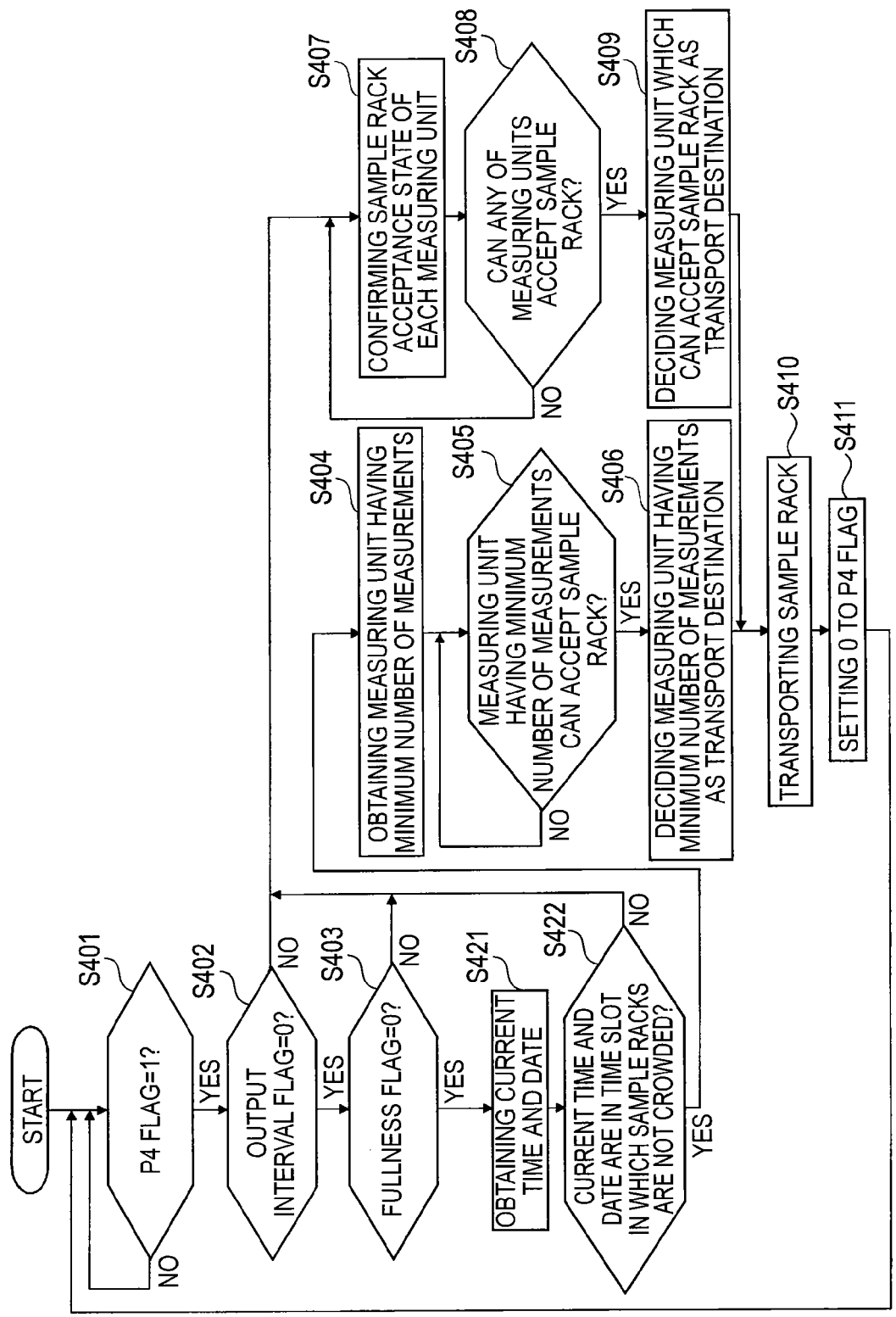
FIG. 12 is a flowchart showing that a sample rack which is positioned at the rear position of a sample insertion unit according to a second embodiment is controlled to be output toward a sample transport unit.

FIG. 12 is a flowchart showing that a sample rack L which is positioned at the position P4 is controlled to be output toward the sample transport unit 3. In FIG. 12, S421 and S422 are added to the flowchart of FIG. 11. Hereinafter, the added processes S421 and S422 will be described only.

When it is determined that a fullness flag is 0 (S403: YES), the CPU 702a of the transport controller 7 obtains current time and date (S421). Next, the CPU 702a determines whether the current time and date which are obtained in S421 are in a time slot in which sample racks L are not crowded on the basis of statistics on the crowded state (S422). When it is determined that the current time and date are in a time slot in which sample racks are not crowded (S422: YES), the process proceeds to S404, and when it is determined that the current time and date are in a time slot in which sample racks are crowded (S422: NO), the process proceeds to S407.

Here, the statistics on the crowded state which are used in S422 will be described.

Figure 13:
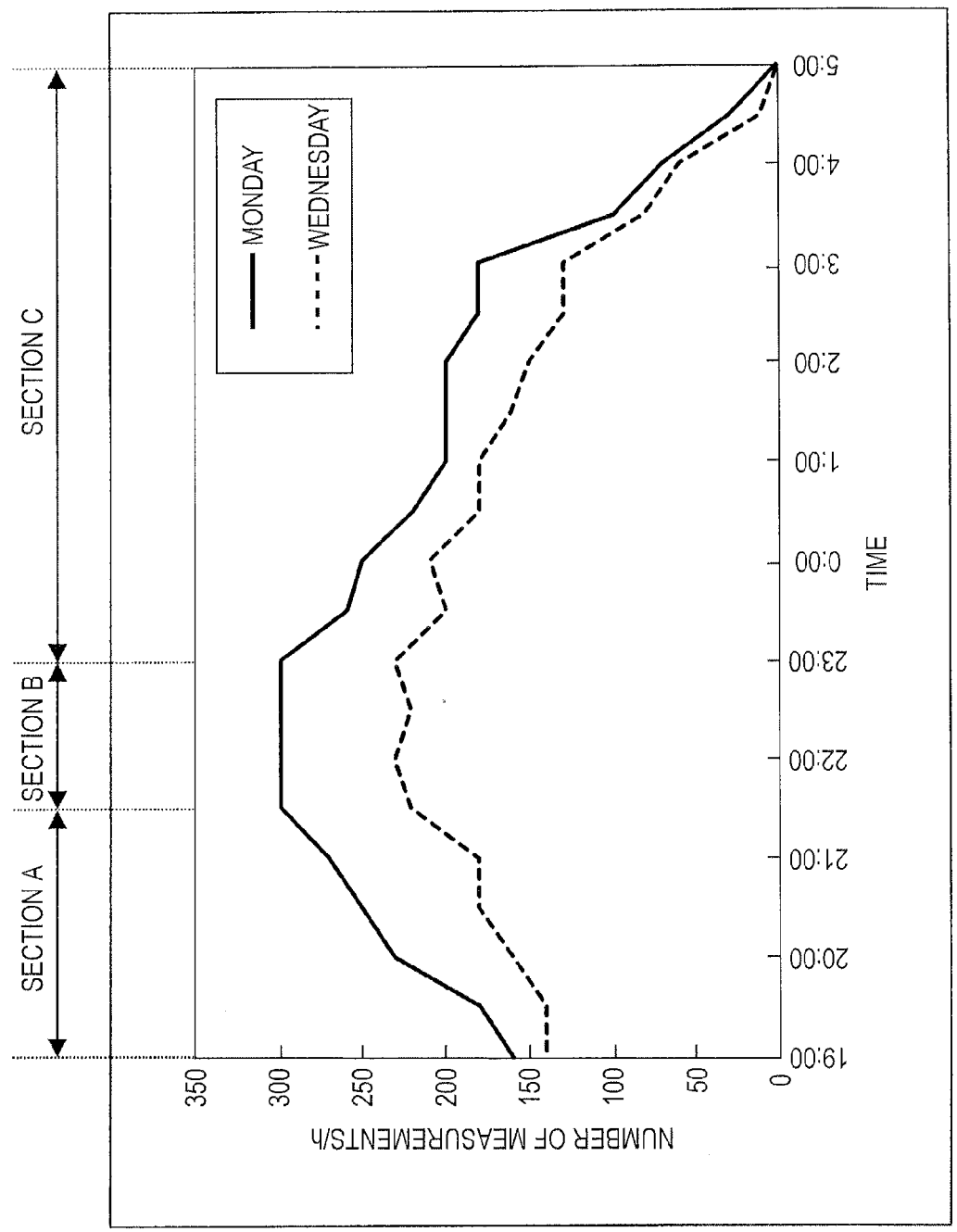
FIG. 13 is a diagram showing statistics on the crowded state of sample racks according to the second embodiment.

FIG. 13 is a diagram showing statistics on the crowded state of sample racks L. In FIG. 13, the horizontal axis indicates a time, and the vertical axis indicates the number of measurements per hour which is performed by the three measuring units 41. In addition, in FIG. 13, for the sake of convenience, only the statistics of Monday and Wednesday are shown.

The statistics on the crowded state of sample racks L shown in FIG. 13 are obtained in the following procedure.

First, the transport controller 7 obtains the number of measurements of each of the three measuring units 41 for every 30 minutes in the use time range (in FIG. 13, 19:00 to 5:00) of the sample analysis system 1, and thus calculates the number of measurements per hour. The number of measurements per hour is stored in the storage section 702b of the transport controller 7. In this embodiment, the maximum value (hereinafter, referred to as "maximum number of measurements") of the number of measurements per hour which is performed by the three measuring units 41 is 300.

The transport controller 7 stores the transition of the number of measurements per hour in the storage section 702b for every day of a week and equalizes the transition of every day of a week stored over a predetermined number of dates for every day of a week. In this manner, the transport controller 7 obtains the statistics on the crowded state as shown in FIG. 13.

Referring to the statistics on the crowded state of Monday of FIG. 13, between 19:00 and 21:30 (section A in FIG. 13) and between 23:00 and 5:00 (section C in FIG. 13), the number of measurements is smaller than the maximum number of measurements per hour. Accordingly, it is found that the three measuring units 41 are not in a state to always perform the measurement (the state in which sample racks L are crowded) in the sections A and C. On the other hand, between 21:30 to 23:00 (section B in FIG. 13), the number of measurements per hour is the maximum number of measurements. Accordingly, it is found that the tree measuring units 41 are in a state to always perform the measurement (the state in which sample racks L are crowded) in the section B.

In this embodiment, for example, on Monday, in addition to the time slot (section B in FIG. 13) in which the number of measurements per hour is the maximum number of measurements, the time slot (section A in FIG. 13) in which the number of measurements per hour reaches the maximum number of measurements is also a time slot in which the three measuring units 41 can be in a state to always perform the measurement (the state in which sample racks L are crowded). The reason for including the section A as well as the section B as a time slot in which sample racks L can be easily crowded on Monday is as follows.

Although the three measuring units 41 are not in a state to always perform the measurement in the section A, the three measuring units 41 have a very high possibility to be in a state to always perform the measurement when the current time enters the section B. Accordingly, in the section A as a time slot in which sample racks L are crowded, when the measuring unit 41 as a transport destination is decided as shown in S407 to S409 of FIG. 12, the measurement can be more smoothly performed when the current time enters the section B.

On Wednesday, since there are no cases in which the number of measurements per hour is the maximum number of measurements, no time slot in which sample racks L are crowded is set.

Returning to FIG. 12, in S422, it is determined whether the current day of week and the current time slot are related to the time slot in which sample racks L are not crowded as described in FIG. 13. For example, when the current day of week is Monday, the determination result is YES in S422 in the case in which the current time is included in the section A or B. However, the determination result is NO in S422 in the case in which the current time is included in the section C. In addition, when the current day of week is Wednesday, the determination result is YES in S422 regardless of the section including the current time.

According to this embodiment, when although the determination result is YES in S402 and S403, it is determined that the current time and date are included in the time slot in which sample racks L are crowded, the sample rack L is transported to the measuring unit 41 which can accept the sample rack L regardless of the number of measurements. Accordingly, a more smooth and efficient transport operation of the sample rack L can be realized.

As described above, the embodiments of the present invention have been described, but are not limited thereto.

For example, in the above-described embodiments, blood is exemplified as a measurement target. However, urine also can be a measurement target. That is, the present invention can also be applied to a sample processing apparatus which examines urine, and further, can be applied to a clinical sample examination apparatus which examines other clinical samples.

In addition, in the above-described embodiments, an example has been described in which sample racks are sorted into the three measuring units 41 of the blood cell analysis apparatus 4. However, the present invention is not limited thereto. A plurality of the smear preparation apparatuses 6 may be connected to sort sample racks into these smear preparation apparatuses 6.

In addition, in the above-described embodiments, a sample rack L is transported to the measuring unit 41 having the minimum number of measurements. However, a sample rack L may be transported to the measuring unit 41 having the smaller number of measurements than any other measuring units 41.

In addition, in the above-described embodiments, a sample rack L is transported to the measuring unit 41 having the minimum number of measurements. However, a sample rack L may be transported to the measuring unit 41 having the minimum number of sample racks L transported to the measuring unit 41.

FIG. 8B is a diagram showing the number of sample racks L which are transported to the measuring unit 41. This number is stored in the storage section 302b of each of the sample transport units 3 and the storage section 702b of the transport controller 7. In addition, in this case, a sample rack L may be transported to the measuring unit 41 having the smaller number of sample racks L transported to the measuring unit 41 than any other measuring units 41.

Further, in this case, as shown in FIG. 8C, the number of measurements of the measuring unit 41 and the number of sample racks L transported to the measuring unit 41 may be stored. In this case, first, a sample rack L is transported to the measuring unit 41 having a small number of measurements of the measuring unit 41, and when the measuring units 41 have the same number of measurements, a sample rack L may be transported to the measuring unit 41 having a small number of sample racks L transported to the measuring unit 41. Otherwise, a sample rack L is transported to the measuring unit 41 having a small number of sample racks L transported to the measuring unit 41, and when the measuring units 41 have the same number of sample racks L transported to the measuring unit 41, a sample rack L may be transported to the measuring unit 41 having a small number of measurements of the measuring unit 41. Otherwise, a weighting α by which the number of measurements of the measuring unit 41 is multiplied and a weighting β by which the number of sample racks L transported to the measuring unit 41 is multiplied will be used. Accordingly, in the measuring units (1) to (3), the measuring unit 41 having the minimum value among ($\alpha$N1+$\beta$M1), ($\alpha$N2+$\beta$M2) and ($\alpha$N3+$\beta$M3) may be decided as a transport destination.

In addition, in the above-described embodiments, the measuring unit 41 which is a transport destination is decided on the basis of the output interval flag and the fullness flag. However, a sensor may be disposed in the sample insertion unit 22 to decide the measuring unit 41 which is a transport destination on the basis of the time interval of a sample rack L which is inserted into the sample insertion unit 22. That is, when the time interval of a sample rack L which is inserted into the sample insertion unit 22 is greater than a predetermined value, the three measuring units 41 may be determined to be in a state in which there is no need to always perform the measurement, that is, in a state in which sample racks L are not crowded, and the processes of S404 to 5406 may be performed. When the time interval of a sample rack L which is inserted into the sample insertion unit 22 is less than the predetermined value, the three measuring units 41 may be determined to be in a state in which it is necessary to always perform the measurement, that is, in a state in which sample racks L are crowded, and the processes S407 to S409 may be performed.

In addition, in the above-described embodiments, how much the sample rack L is interrupted behind the position P4 on the transport passage 231 of the sample output unit 23 is determined by the number of pulses which are applied to the stepping motor of the rack input mechanism 235. However, a sensor may be disposed in the sample output unit 23 to detect the number of sample racks L which are on the transport passage 231 to thereby determine how much the sample rack L is interrupted.

In addition, in the above-described embodiments, an output interval of a sample rack L, caused by the rack output mechanism 223 of the sample insertion unit, is used as an output interval. However, an output interval of a sample rack L, caused by the rack output mechanism 237 of the sample output unit 23, may be used. In addition, a reading interval of a bar-code label BL2 of a sample rack L, caused by the bar-code reading section 233 or 238, also may be used.

In addition, in the above-described embodiments, when the plural measuring units 41 can accept a sample rack L in S407 to S409, the sample rack L is transported to the measuring unit 41 on the downstream side. However, the sample rack L may be transported to the measuring unit 41 which can accept the sample rack L as rapidly as possible.

In this case, for example, when it is determined whether there is a sample rack L during the measurement or yet to be measured on the rack transport section 320 of the sample transport unit 3 and there is no sample rack L during the measurement or yet to be measured on the transport section 320, a sample rack L can be accepted more rapidly.

Further, when there is a sample rack L during the measurement or yet to be measured on the rack transport section 320, the measuring unit 41 in which the suction of all the sample containers T held in a sample rack L is most rapidly completed by the sample suction section 413 can accept the sample rack L more rapidly. Whether the suction of all the sample containers T is most rapidly completed is judged by, for example, the number of sample containers T yet to be measured. In addition, when there is a sample rack L during the measurement on the rack transport section 320, the measuring unit 41 in which the uptake of all the sample containers T held in the sample rack L is most rapidly completed by the hand section 411a of the measuring unit 41 can accept the sample rack L more rapidly. At this time, the sample rack L may be transported to the measuring unit 41 which can accept the sample rack L more rapidly than any other measuring units 41.

In addition, in the above-described second embodiment, as in the case of Monday of FIG. 13, the section B in which the number of processed samples per hour is maximum and the section A in which the number of processed samples reaches the section B are a time slot in which sample racks L are crowded. However, only the section B may be a time slot in which sample racks L are crowded. In addition, the section B and a predetermined duration before and after the section B may be a time slot in which sample racks L are crowded. In addition, when there is a plurality of sections in which the number of processed samples per hour is maximum in one day, sections between these sections also may be a time slot in which sample racks L are crowded. In addition, an operator may set a time slot in which sample racks L are crowded.

In addition, in the above-described embodiments, the measuring unit 41 mixes a sample which is contained in a sample container T and reagents which are contained in the reagent containers 441 to 443 during the measurement. Accordingly, the number of measurements of the measuring unit 41 and the amount of reagents consumed by the measuring unit 41 have a proportional relationship. Accordingly, determining the measurement load on the measuring unit 41 by the number of measurements of the measuring unit 41 and determining measurement load on the measuring unit 41 by the amount of reagents consumed by the measuring unit 41 have an equivalence relationship. Accordingly, the number of measurements of the Claim 6 can be said to be substantially the same as the amount of reagents consumed, and includes other parameters having an equivalence relationship with the number of measurements and the amount of reagents consumed.

In addition, in the above-described embodiments, when receiving the rack ID of a sample rack L, the sample ID of a sample container T and the holding position of the sample container T from the sample output unit 23, the transport controller 7 inquires of the host computer 8 for a measurement order. However, the present invention is not limited thereto. Measurement data corresponding to sample IDs may be stored in the storage section 702b of the transport controller 7, and when the transport controller 7 receives the above-described data from the sample output unit 23, the transport controller 7 may read out measurement data corresponding to the received sample ID from the storage section 702b and transmit it to the sample output unit 23.

In addition, in the above-described embodiments, the sample recovery unit 21 is disposed on the right side of the sample insertion unit 22. However, it may be disposed on the left side of the sample transport unit 5. In this case, a sample rack L in which analysis or preparation of a smear has been completed is output to the left side of the sample transport unit 5 along the transport line L2 and recovered by the sample recovery unit 21.

In addition, in the above-described embodiments, the transport controller 7 decides whether to transport a sample rack L to the measuring unit 41 having the minimum number of measurements or the measuring unit 41 capable of accepting a sample rack on the basis of the output interval flag and the fullness flag. However, the present invention is not limited thereto. The transport controller 7 may include a display section to display a reception screen for receiving the selection of whether to transport the sample rack to the measuring unit 41 having the minimum number of measurements or the measuring unit 41 capable of accepting the sample rack on the display section, and an operator may select a transport method of the sample rack L via the reception screen. The reception screen also may be a screen for selecting and setting one of a mode which gives priority to a reduction in the measurement load on the measuring unit and a mode which gives priority to rapidity of the measurement of the sample.

Various modifications can be made in the embodiments of the present invention within the scope of the technical thoughts which are shown in the claims.

What is claimed is:

1. A sample processing apparatus comprising:
   a plurality of sample processing units, each processing a sample contained in a sample container;
   a transport apparatus that transports a sample rack holding a sample container to at least any one of the plurality of sample processing units;
   a rack feeding section that receives a sample rack and feeds the received sample rack to a transport line of the transport apparatus; and
   a controller configured to instruct the transport apparatus to transport a sample rack fed by the rack feeding section to (a) a sample processing unit which can accept a subsequent sample rack more rapidly than any other sample processing unit when a quantity of sample racks received by the rack feeding section is not smaller than a predetermined quantity, and instruct the transport apparatus to transport a sample rack fed by the rack feeding section to (b) a sample processing unit having a lower processing load than any other sample processing unit when a quantity of sample racks received by the rack feeding section is smaller than a predetermined quantity.

2. The sample processing apparatus according to claim 1, wherein the controller obtains a number of times that each of the sample processing units had implemented a processing of a sample, and
   the sample processing unit having the lower processing load than any other sample processing unit is a sample processing unit which had implemented a processing of a sample at the smallest number of times among the plurality of sample processing units.

3. The sample processing apparatus according to claim 1, wherein the controller obtains a number of sample racks transported to each of the sample processing units, and
   the sample processing unit having the lower processing load than any other sample processing unit is a sample processing unit to which the smallest number of sample racks had been transported among the plurality of sample processing units.

4. The sample processing apparatus according to claim 1, comprising:
   a receiving part which receives a selection of whether to set (i) a first transport method for transporting the sample rack fed by the rack feeding section to the sample processing unit which can accept the subsequent sample rack more rapidly than any other sample processing unit or (ii) a second transport method for transporting the sample rack fed by the rack feeding section to the sample processing unit having the lower processing load than any other sample processing unit,
   wherein the controller instructs the transport apparatus to transport the sample rack fed by the rack feeding section by a transport method received by the receiving part.

5. The sample processing apparatus according to claim 4, further comprising a display section for displaying a reception screen for selecting whether to set (i) the first transport method or (ii) the second transport method.

6. The sample processing apparatus according to claim 1, comprising a rack set section on which a sample rack is set by a user and which transfers the set sample rack to the rack feeding section,
wherein when a reception interval at which the rack feeding section receives sample racks is not greater than a predetermined interval, the controller instructs the transport apparatus to transport the sample rack fed by the rack feeding section to (a) the sample processing unit which can accept the subsequent sample rack more rapidly than any other sample processing unit, and
when the reception interval is greater than the predetermined interval, the controller instructs the transport apparatus to transport the sample rack fed by the rack feeding section to (b) the sample processing unit having the lower processing load than any other sample processing unit.

7. The sample processing apparatus according to claim 6, wherein the rack feeding section includes a storage section that stores the received sample rack before feeding the sample rack to the transport line,
when the reception interval is greater than the predetermined interval and a number of sample racks stored in the storage section is not smaller than a predetermined number, the controller instructs the transport apparatus to transport the sample rack fed by the rack feeding section to (a) the sample processing unit which can accept the subsequent sample rack more rapidly than any other sample processing unit, and
when the reception interval is greater than the predetermined interval and the number of the sample racks stored in the storage section is smaller than the predetermined number, the controller instructs the transport apparatus to transport the sample rack fed by the rack feeding section to (b) the sample processing unit having the lower processing load than any other sample processing unit.

8. The sample processing apparatus according to claim 6, wherein the rack feeding section includes a detector that detects an identification information of the received sample rack, and
the reception interval is an interval of detecting by the detector.

9. The sample processing apparatus according to claim 6, wherein when a current time is included in a time slot in which a crowded state of the sample racks set in the rack set section is severe, the controller instructs the transport apparatus to transport the sample rack fed by the rack feeding section to (a) the sample processing unit which can accept the subsequent sample rack more rapidly any other sample processing unit, even when the reception interval is greater than the predetermined interval.

10. The sample processing apparatus according to claim 6, wherein the transport line of the transport apparatus comprises at a respective sample processing unit:
a sample supply line configured to transport a sample rack to supply a sample in the sample rack to a corresponding sample processing unit; and
a bypass line that separates from the sample supply line and configured to transport a sample rack to pass through the corresponding sample processing unit or to transfer the sample rack to the corresponding sample supply line, and
when the reception interval is not greater than a predetermined interval, the controller instructs the transport apparatus to transport a subsequent sample rack to a sample processing unit corresponding to a sample supply line on which there is no sample rack fed by the rack feeding section.

11. A sample processing apparatus comprising:
a plurality of sample processing units, each processing a sample contained in a sample container;
a transport apparatus that transports a sample rack holding a sample container to at least any one of the plurality of sample processing units;
a rack feeding section that receives the sample rack and feeds the received sample rack to a transport line of the transport apparatus; and
a controller configured to instruct the transport apparatus to transport a sample rack fed by the rack feeding section to(a) a sample processing unit which can accept a subsequent sample rack more rapidly than any other sample processing unit when a current time is included in a time slot in which a crowded state of sample racks set in the sample processing apparatus is severe, and to instruct the transport apparatus to transport a sample rack fed by the rack feeding section to (b) a sample processing unit having a lower processing load than any other sample processing unit when the current time is not included in the time slot.

12. The sample processing apparatus according to claim 11,
wherein the transport line of the transport apparatus comprises at a respective sample processing unit:
a sample supply line configured to transport a sample rack to supply a sample in the sample rack to a corresponding sample processing unit; and
a bypass line that separates from the sample supply line and configured to transport a sample rack to pass through the corresponding sample processing unit or to transfer the sample rack to the corresponding sample supply line, and
when the current time is included in the time slot, the controller instructs the transport apparatus to transport a subsequent sample rack to a sample processing unit corresponding to a sample supply line on which there is no sample rack fed by the rack feeding section.

13. The sample processing apparatus according to claim 11,
wherein the controller obtains a number of times that each of the sample processing units had implemented a processing of a sample, and
when the current time is not included in the time slot, the controller instructs the transport apparatus to transport the sample rack fed by the rack feeding section to a sample processing unit which had implemented a processing of a sample at the smallest number of times.

14. The sample processing apparatus according to claim 11,
wherein the controller obtains a number of sample racks transported to each of the sample processing units, and
when the current time is not included in the time slot, the controller instructs the transport apparatus to transport the sample rack fed by the rack feeding section to a sample processing unit to which the smallest number of sample racks had been transported among the plurality of sample processing units.

15. The sample processing apparatus according to claim 11, further comprising:
a receiving part which receives a selection of whether to set (i) a first transport method for transporting the sample rack fed by the rack feeding section to the sample processing unit which can accept the subsequent sample rack more rapidly than any other sample processing unit or (ii) a second transport method for transporting the sample rack fed by the rack feeding section to the sample processing unit having the lower processing load than any other sample processing unit, wherein the controller instructs the transport apparatus to transport the sample rack fed by the rack feeding section by a transport method received by the receiving part.

16. The sample processing apparatus according to claim 11, comprising a rack set section on which a sample rack is set by a user and which transfers the set sample rack to the rack feeding section, wherein when an reception interval at which the rack feeding section receives sample racks is not greater than a predetermined interval, the controller instructs the transport apparatus to transport the sample rack fed by the rack feeding section to (a) the sample processing unit which can accept the subsequent sample rack more rapidly than any other sample processing unit even when the current time is not included in the time slot.

17. The sample processing apparatus according to claim 16, wherein the rack feeding section includes a storage section that stores the received sample rack before feeding the sample rack to the transport line, and when the reception interval is greater than a predetermined interval and a number of sample racks stored in the storage section is not smaller than a predetermined number, the controller instructs the transport apparatus to transport the sample rack fed by the rack feeding section to(a) the sample processing unit which can accept the subsequent sample rack more rapidly than any other sample processing unit even when the current time is not included in the time slot.

18. A sample rack transporting method by a sample processing apparatus comprising:

receiving a sample rack holding a sample container;

feeding the received sample rack to a transport line of the sample processing apparatus;

transporting the fed sample rack to (a) a sample processing unit which can accept a subsequent sample rack more rapidly than any other sample processing unit when a quantity of the fed sample racks is not smaller than a predetermined quantity and transporting the fed sample rack to (b) a sample processing unit having a lower processing load than any other sample processing unit when a quantity of the fed sample racks is smaller than a predetermined quantity.

19. A sample rack transporting method by a sample processing apparatus comprising:

receiving a sample rack holding a sample container;

feeding the received sample rack to a transport line of the sample processing apparatus;

transporting the fed sample rack to either (a) a sample processing unit which can accept a subsequent sample rack more rapidly than any other sample processing unit or (b) a sample processing unit having a lower processing load than any other sample processing unit, when the current time is included in a time slot in which a crowded state of the sample racks set in the sample processing apparatus is severe.

* * * * *